United States Patent
Jennewein et al.

(10) Patent No.: US 10,011,821 B2
(45) Date of Patent: Jul. 3, 2018

(54) MELLEOLIDE-BIOSYNTHESIS GENE CLUSTER AND ITS APPLICATIONS

(71) Applicant: Fraunhofer-Gesellschaft zur Foerderung der angewandten Forschung e. V., Munich (DE)

(72) Inventors: Stefan Jennewein, Bad Honnef (DE); Benedikt Engels, Aachen (DE)

(73) Assignee: Fraunhofer-Gesellschaft zur Foerderung der angewandten Forshung e. V., Munich (DE)

( * ) Notice: Subject to any disclaimer, the term of this patent is extended or adjusted under 35 U.S.C. 154(b) by 0 days.

(21) Appl. No.: 15/190,052

(22) Filed: Jun. 22, 2016

(65) Prior Publication Data

US 2016/0319251 A1    Nov. 3, 2016

Related U.S. Application Data

(63) Continuation of application No. PCT/EP2014/050246, filed on Jan. 8, 2014.

(51) Int. Cl.
| | |
|---|---|
| *C12N 9/02* | (2006.01) |
| *C12N 15/52* | (2006.01) |
| *C12P 7/18* | (2006.01) |
| *C12P 7/62* | (2006.01) |
| *C12P 15/00* | (2006.01) |

(52) U.S. Cl.
CPC ........... *C12N 9/0071* (2013.01); *C12N 15/52* (2013.01); *C12P 7/18* (2013.01); *C12P 7/62* (2013.01); *C12P 15/00* (2013.01); *C12Y 114/14001* (2013.01)

(58) Field of Classification Search
CPC ................................. C12N 9/0077; C12P 1/04
USPC .............................................. 435/189, 252.3
See application file for complete search history.

(56) References Cited

U.S. PATENT DOCUMENTS 7,553,648 B2 *   6/2009   Hauer ................... C12N 9/0077
                                                           435/132

FOREIGN PATENT DOCUMENTS

| JP | 2009-511020 A | 3/2009 |
| JP | 2011-055721 A | 3/2011 |
| JP | 2013-510573 A | 3/2013 |
| WO | WO 2005/030806 A2 | 4/2005 |
| WO | WO 2007/044688 A1 | 4/2007 |
| WO | WO 2011/060057 A1 | 5/2011 |
| WO | WO 2012/016912 A1 | 2/2012 |

OTHER PUBLICATIONS

Bok et al., "Chimpanzees as an animal model for human norovirus infection and vaccine development," *PNAS* 108(1): 325-330 (Jan. 4, 2011).
Chachu et al., "Antibody is critical for the clearance of murine norovirus infection," *Journal of Virology* 82(13): 6610-6617 (Jul. 1, 2008).
Chen et al., "Development of Norwalk virus-specific monoclonal antibodies with therapeutic potential for the treatment of Norwalk virus gastroenteritis," *Journal of Virology* 87(17):9547-9557 (Sep. 1, 2013).
Czakó et al., "Serum hemagglutination inhibition activity correlates with protection from gastroenteritis in persons infected with norwalk virus," *Clinical and Vaccine Immunology* 19(2): 284-287 (Feb. 2012).
Ettayebi et al., "Recombinant norovirus-specific scFv inhibit virus-like particle binding to cellular ligands," *Virology Journal* 5(1): 1-8 (Jan. 31, 2008).
International Search Report from parent PCT Application No. PCT/US2014/015809, 9 pages (dated Jul. 9, 2014).
Para et al., "Multiple antigenic sites are involved in blocking the interaction of GII.4 norovirus capsid with ABH histo-blood group antigens," *Journal of Virology* 86(13): 7414-7426 (Jul. 1, 2012).
Written Opinion from parent PCT Application No. PCT/US2014/015809, 11 pages (dated Jul. 9, 2014).
Dimster-Denk et al., "Feedback regulation of 3-hydroxy-3-methylglutaryl coenzyme a reductase in *Saccharomyces cerevisiae*," *Molecular Biology of the Cell* 5(6):655-665 (Jun. 1, 1994).
Engels et al., "Cloning and characterization of an armillaria gallica cDNA encoding protoilludene synthase, which catalyzes the first committed step in the synthesis of antimicrobial melleolides," *Journal of Biological Chemistry* 286(9): 6871-6878 (Mar. 4, 2011).
Engels et al., "Metabolic engineering of taxadiene biosynthesis in yeast as a first step towards Taxol (Paclitaxel) production," *Metabolic Engineering* 10(3-4): 201-206 (May-Jul. 2008).
International Search Report from parent PCT Application No. PCT/EP2014/050246, 9 pages (dated Nov. 14, 2014).
Jennewein et al., "Coexpression in yeast of taxus cytochrome P450 reductase with cytochrome P450 oxygenases involved in Taxol biosynthesis," *Institute of Biological Chemistry* 89(5): 588-598 (epub Jan. 25, 2005).
Murray and Thompson, "Rapid isolation of high molecular weight plant DNA," *Nucleic Acids Research* 8(19): 4321-4326 (1980).
Quin et al., "Mushroom hunting by using bioinformatics: application of a predictive framework facilitates the selective identification of sesquiterpene synthases in Basidiomycota," *ChemBioChem* 14(18): 2480-2491 (2013).
Written Opinion from parent PCT Application No. PCT/EP2014/050246, 10 pages (dated Nov. 14, 2014).

* cited by examiner

*Primary Examiner* — Tekchand Saidha
(74) *Attorney, Agent, or Firm* — Klarquist Sparkman, LLP

(57) ABSTRACT

The present invention relates to the production of hydroxylated protoilludenes and/or sesquiterpenoid protoilludene-type aryl esters using newly identified genes that can be employed. The present invention accordingly relates to a host microorganism that has been transformed with the newly identified nucleotide sequences and to methods employing the transformed microorganism.

23 Claims, 7 Drawing Sheets

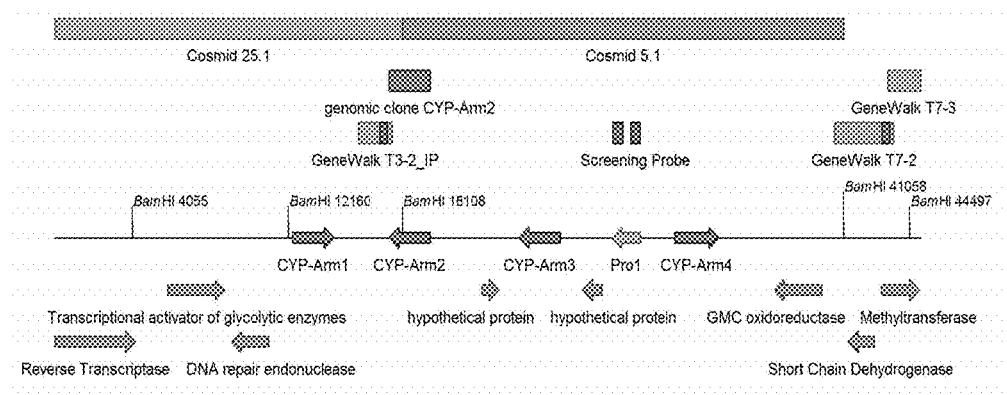

Fig. 2A

SEQ ID NO: 1 CYP-Arm1
MALFSAYALAFSLLMVPLILYILRIGRRESGLPPGPSTLPLVGNLHQLPHGSLHLQFTAWAKEFGGIF
SLKFGPGTVIVATSPRAVRELIDQKSASTSDRPPSHFSNVITGGNNIGFARYSDYWRRGRRVMHS
MLTKKACVNHLTIQRAEASQLMYDYLVEPKVNLSHQILVANVGKSDVQCQEFVAHGQRYANSVITS
ILAGTRSPHHTSPLVTAFFQMQHEWTHLLTPGAHPPVDMVPFLKYIPGSWKQICAKMKVSQEELY
GGMIDACAKRVERGIRNGCFLEGELENKDVDRGLLRGMCSALMEGGSDSTSIYLQSFILMLVAHP
DVQAKARAEIDSVVGLDRLPDIEDMDNLPYVSAVIKEVLRLRPITALGAPHYSTQPEVVDGYVIPKN
SMIFMNQWGMLHDPDSYDQPESFMPERFLTSPFGTRPGADDTGRSKDIYFGGGRRICVGMHFG
QNSLAITSMYLIWAFNLTNAIDPQTKNPIPVDINEYDISLNTIPKPFKCDFQVRSEEHKRMVENAFAE
SRQVLAPFEQD

Fig. 2B

SEQ ID NO: 2 CYP-Arm2
MTHASSAWFLAAVAIVTFIVVRRIRSSWRKLPPGPRGLPIVGNLLQLRSKQWLTFTELGKKYGDLM
YFNVAGQPLIVINSLRVATDLLDRAKFSDRPRNIVASDIMTRGMFVAFAPYGNAWRHMRKAAHEGL
NKNIVNQYHPIQIKEAVLLANDLLAEPNRWVSHVRRTAASTIMSIVYDKPATSEQDPSIKRINDFAAR
LTRAAMPGAHFVESFPWMLRIPSKYAKWKREAEGWYAKDSSMFESLFHSVKDRVAEGNNRPSFV
ATLIQGAGRHGLTDHESSWLAGAMYTAGVESSSAAISWWMLAMILYPDAQKRAQAELDKVVGRD
RLPAFSDYEHLPYVRAMVKETLRWRAVDPVGLPHRSTEDDIYNGYFIPAGSILIANVWHINRDPEN
YGLDAEHFDPARHLDETGQLAPVAGTKEENHVSFGFGRRICVGRHIANDTLFAVIATLLWAIHIEPA
TDEKGASLPLDVDGCIEDGVVVRPLPFKVKVTPRFSEAQAIVEQERELLGHY

Fig. 2C

SEQ ID NO: 3 CYP-Arm3
MTRIFSEEVSPIWILTAIVVVAYTTVRYLRSPWRNLPPGPRGLPLIGNLLELRGKQWLTFTELGKKY
GDLMYFNVAGQPLVVLNSQKVAADLLDRRAGKYSDRPRNIVASDIMTGGNLVVFTRYGDVWRRM
RKAAHEGLNKGVVYKYHPIQTAEAVLLTAGVLAEPEKWNSHLRRTAASAIMSMVYDTPPTSEQDP
SVKNINEFVARLTRAAMPGAHFVEFFPWMRYIPSKYAKWKREAEESYAKDSAMFEGLFNGVKDR
VAKGDERPSLASTLIQDAGRHDLTDRENSWLAGTMYAAGAETTSGVMSWWTLAMIVYPETQKRA
QAELDAVVGRDRLPSFADYEHLPYIRAMVKEALRWRMVDPVGLPHTSTEDDVYDGYFIPAGTIIAN
VWHLNRDPEIYGPDAEHFNPARHLDKDGKLAPGPADTKEESHVTYGFGRRICVGRHVANNSLFIDI
AMMLWAMNIERATDENGVPLPLDVDGCVEDGLVTRPVPFKAKITPRFREAQAIVEQERELLGYH

Fig. 2D

SEQ ID NO: 4 CYP-Arm4
MDSASLAVVVWAILLVLWLRRIFGQRSSLPLPPAPPGYPVIGNLLDLANNDVHIRARHWSRNFDDD
VISLKVLGKTMIILNSPTAVSDLFDKRASNYSDRPDMPMIVDLMGWDWTFALMRYGPRWKEHRRV
FNNHFNIGTSGASEDRHIQLRICRELLSLMFQSPSKYLENLRHYTGHIILKRTYGHTVVDEKDPYIRL
VEAASQSTSEAAVPGAFLVDLFPSMKYIPEWVPGAQFKRKAREWRKLSEAMINAPYDMAKGKFD
EGNAEPCFVSACLEQNKTASGQGLSEELIKDTAAVAYAAGADTSVSTLTTFILAMTLYPDVQKAAQ
AELDALLGGERLPDFGDKTRLPYVTAILKEVLRWIPVLPMAVPHRAVNADTYKGYYIPAGAFVYGN
AWAILHNPDIFADPETFRPDRFIENPTLLNPIDNGVFGFGRRACAGRVMALDTMWIAMASILAVFDI
SKAVDERGNEISPPVKLSPGTISHPAPFPCIIKPRSKAALELITQDD

Fig. 2E

MELLEOLIDE-BIOSYNTHESIS GENE CLUSTER AND ITS APPLICATIONS

CROSS-REFERENCE TO RELATED APPLICATIONS

This application is a continuation of Patent Cooperation Treaty (PCT) Patent Application No. PCT/EP2014/050246, filed on Jan. 8, 2014, designating the U.S., which was published in English, and which is incorporated herein by reference in its entirety.

The present invention relates to a newly identified gene cluster, in particular to newly identified polynucleotides within said gene cluster, as well as to the polypeptides encoded by the polynucleotides, and to their production and uses, as well as their variants and their uses. In addition, the present invention relates to a method for producing hydroxylated protoilludene and/or sesquiterpenoid protoilludene-type aryl esters by using the newly identified polynucleotides/polypeptides.

BACKGROUND

Due to the fact that the prevalence of microbial pathogens with resistance towards standard antibiotic therapy constantly increases, research has started to focus on the search and development of new antimicrobial drugs with novel modes of action. Natural products are traditionally a rich source of bioactive compounds, but although terpenoids are by far the largest class of natural products there are only three approved antimicrobial drugs in the terpenoid family and all three are semisynthetic derivatives of the fungal natural product pleuromutilin (tiamulin, valnemulin and retapamulin).

Basidiomycetes are a particularly rich source of complex, structurally diverse, and bioactive sesquiterpenoids, and certain protoilludene-type sesquiterpenoid aryl esters from the genus *Armillaria* are promising leads for the development of new antimicrobial drugs. The genus *Armillaria*, also commonly known as the honey mushroom, is currently classified in the family Physalacriaceae and comprises more than 600 species worldwide. *Armillaria* species are regarded not only as edible mushrooms, but also as notorious root pathogens attacking hardwood trees and conifers, as well as fruit trees and grapevine.

Member of the genus *Armillaria* are known for the production of two types of sesquiterpenoid protoilludene type aryl esters, which are divided according to the position of the double bond into armillylorsellinates and melleolides. Today more than 50 armillylorsellinate and melleolide structures are known from *Armillaria* spp., which makes them one of the most diverse groups of natural products known from fungi.

Whilst the biosynthesis of some terpenes, in particular of plants origin—like menthol, artemisinin or taxol—have been extensively studied in the past, little is known about the synthesis of the vast majority, in particular of terpenes produced by fungi.

Protoilludene type aryl esters are built from a sesquiterpenoid protoilludanol alcohol and orsellinic acid derived aromatic moiety. The biosynthesis of all melleolide and armillylorsellinate type sesquiterpenoids are thought to be derived from the cyclization of the universal sesquiterpene precursor farnesyl-diphosphate to protoilludene. The protoilludene ring system is then subject to several hydroxylation reactions, and the resulting protoilludanol alcohols are then subject to esterification at the C5-hydroxy position with polyketide orsellinic acid derivatives.

Whereas orsellinic acid and derivatives are biosynthesized by numerous microorganisms, and protoilludenes are widespread in homobasidiomycetes, the coupling of both seems to be unique to the genus *Armillaria*.

SUMMARY OF THE INVENTION

Since, as mentioned already above, melleolides and armillyloresellinates, in medicine, are of high interest due to their potential antimicrobial and cytotoxic activity, it would be desirable to have them specifically produced or enriched in a controlled way.

Thus, it is an object of the present invention to provide for new and improved tools by means of which a targeted production, either homologous or heterologous, can be achieved.

According to the invention, this and other objects are achieved by providing an isolated or synthetic or recombinant polynucleotide encoding a polypeptide with cytochrome-P450 monooxygenase activity and comprising or consisting of a nucleic acid sequence selected from the group consisting of: a) SEQ ID NOs: 5 to 8 of the attached sequence listing; b) a nucleic acid sequence complementary to SEQ ID NOs: 5 to 8; c) nucleic acid sequences which hybridize under stringent conditions to the nucleic acid sequences defined in a) and b) or their complementary strands.

In particular, this and other objects are further solved by a gene cluster comprising or consisting of the following genes: *Armillaria gallica* cytochrome-P450-monooxygenase 1, *Armillaria gallica* cytochrome-P450-monooxygenase 2, *Armillaria gallica*-P450-monooxygenase 3, *Armillaria gallica* protoilludene synthase, *Armillaria gallica* cytochrome-P450-monooxygenase 4, wherein the genes are arranged in the order as mentioned.

The objects are further achieved by the use of said polynucleotides or the polypeptides encoded by the polynucleotides for producing a hydroxylated protoilludene or a sesquiterpenoid protoilludene-type aryl ester, and by a respective method for producing a hydroxylated protoilludene and/or a sesquiterpenoid protoilludene-type aryl ester.

Also, the invention provides for the use of the above mentioned gene cluster for producing a hydroxylated protoilludene or a sesquiterpenoid protoilludene-type aryl ester, and by a respective method using the gene cluster for producing a hydroxylated protoilludene and/or a sesquiterpenoid protoilludene-type aryl ester.

The objects are completely achieved in that way.

The above mentioned polynucleotides, each encode an *Armiallaria gallica* polypeptide with monooxygenase activity, which has—according to the inventors' knowledge—been identified, purified and enzymatically characterized for the first time. These newly identified polynucleotides catalyze hydroxylation reactions converting 6-protoilludene into mono- or multiple hydroxylated 6-protoilloudene, the reaction of which represents a crucial step in the synthesis of hydroxylated protoilludenes or sesquiterpenoid protoilludene-type aryl esters. Thus, by having identified the gene encoding the monooxygenases, a valuable and effective tool has been found and generated to influence the production of hydroxylated protoilludenes or sesquiterpenoid protoilludene-type aryl esters: the genes can, either single or in a cluster also comprising protoilludene synthase, heterologously expressed or overexpressed in order to generate multiple copies of said genes, by means of which the cyclization rate and the generation of hydroxylated protoilludenes in the synthesis of sesquiterpenoid protoilludene-type aryl esters is elevated, and, thus, increasing the production of sesquiterpenoid protoilludene-type aryl esters. In that way, highly enriched hydroxylated protoilludenes or sesquiterpenoid protoilludene-type aryl esters may be gained, which can either be used as potent antimicrobial and cytotoxic substances and may be used as therapeutic tools in all different fields of treatment and medicine, or which can be further modified to yield other antimicrobial substances derived from said hydroxylated protoilludenes or sesquiterpenoid protoilludene-type aryl esters.

BRIEF DESCRIPTION OF THE DRAWINGS

Several embodiments of the invention are illustrated in the figures and explained in more detail in the following description. In the figures:

FIGS. 2A-2E show a scheme of the terpene biosynthesis part of the melleolide gene cluster; the cluster contains the protoilludene synthase, four cytochrome-P450-monooxygenases and two hypothetic proteins (FIG. 2A); FIGS. 2B to 2E display the sequences of the four identified cytochrome-P450-monooxygenases;

SEQUENCE LISTING

Figure 1:
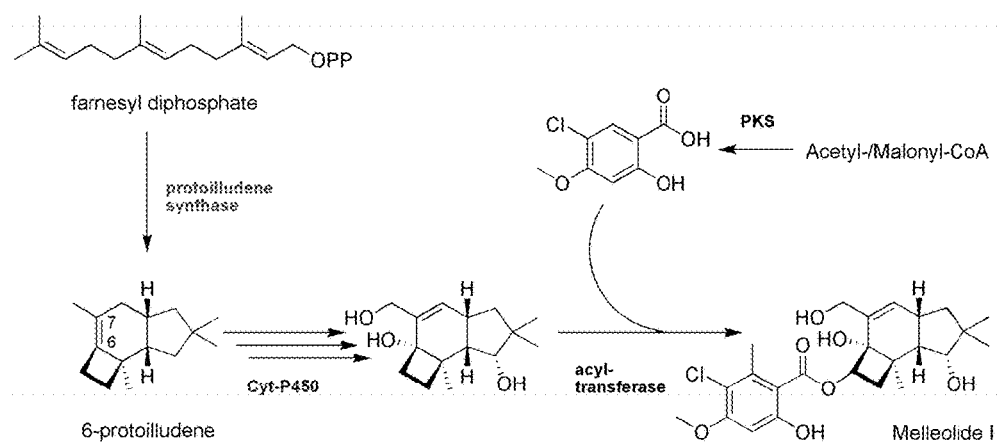
FIG. 1 shows a scheme of melleolide I synthesis involving terpene biosynthesis part starting with cyclization of farnesyldiphosphate to 6-protoilludene, followed by oxygenation via cytochrome-P450-monooxygenases; final step is the attachment of orsellinic acid obtained from polyketide biosynthesis by an acyltransferase.

The Sequence Listing is submitted as an ASCII text file [7291-97169-01_Sequence_Listing.txt, Jun. 21, 2016, 56.5 KB], which is incorporated by reference herein.

DETAILED DESCRIPTION OF SEVERAL EMBODIMENTS

According to the present invention, the term "polynucelotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. Also, "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Similarly, a "synthetic" sequence, as the term is used herein, means any sequence that has been generated synthetically and not directly isolated from a natural source. "Recombinant" means genetically engineered DNA prepared by transplanting or splicing genes from one species into the cells of a host organism of a different species. Such DNA becomes part of the host's genetic makeup and is replicated.

The term "polynucleotide encoding a polypeptide" as used herein encompasses polynucleotides that include a sequence encoding a polypeptide of the invention, particularly monooxygenases of *Armillaria gallica*, having the amino acid sequences as set forth in SEQ ID NOs: 1 to 4. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Also included within the present invention and/or in the definition of variant polypeptide are "orthologous" polypeptides (orthologs), which are peptides encoded by genes in different species that evolved from a common ancestral gene by speciation. Normally, orthologs retain the same function in the course of evolution.

In addition, the term "Host cell" or "host microorganism" is presently defined as a cell or microorganism or microorganism cell, which has been transformed or transfected, or is capable of transformation or transfection by an exogenous polynucleotide sequence, thus heterologously expressing the introduced polynucleotide.

Presently and as generally understood, a "sesquiterpenoid protoilludene-type aryl ester" is to be understood to represent either an armillyloresellinate or a melleolide. As such, they are built from an oxygenated sesquiterpenoid protoilludene and orsellinic acid.

According to an embodiment of the invention, the isolated polynucleotide consists of one the SEQ ID NOs: 5 to 9 of the attached sequence listing and encodes a polypeptide with monooxygnease activity (SEQ ID NOs: 5 to 8) or represents a gene cluster comprising 4 monooxygenases and protoilludene synthase. SEQ ID NOs: 5 to 8 represent the sequences of four different *Armillaria gallica* monooxygenases contained in the newly identified melleolides synthesis gene cluster of *Armillaria gallica*, which cluster also comprises the protoilludene synthase gene. SEQ ID NO: 9 shows the sequence of the cluster.

SEQ ID NOs: 5 to 8 as disclosed in the attached sequence listing are the four cDNA sequences, respectively, of the monooxygenases 1 to 4 as identified and characterized from *Armillaria gallica*. It is to be understood that also variants thereof, which have at least a sequence identity of 90%— and that might even be found in other *Armillaria* species— are also suitable and part of the invention, since with the newly identified monooxygenases valuable tools are provided by means of which similar monooxygenases, i.e. monooxygenases that slightly differ from SEQ ID NOs: 5 to 8, may be identified by sequence comparison and subsequent enzymatically testing.

The invention also relates to vectors that comprise a polynucleotide or polynucleotides of the invention, host microorganisms and/or host cells that are genetically engineered with vectors of the invention and the production of polypeptides of the invention by recombinant techniques.

Cell-free translation systems can also be employed to produce such polypeptides using RNAs derived from the DNA constructs of the invention.

Thus, and in addition, the invention also concerns a vector, containing a nucleic acid sequence as defined above, encoding a polypeptide with monooxygenase activity, the nucleic acid sequence being operably linked to control sequences recognized by a host cell/microorganism transformed or transfected with the vector. According to one aspect of the invention, the vector is an expression vector, and, according to another aspect, the vector can be present in the form of a plasmid, cosmid, phage, liposome, or virus.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., Basic Methods in Molecular Biology, (1986), and Sambrook et al., Molecular Cloning: A Laboratory Manual, 2nd Ed., Cold Spring Harbor Laboratory Press, Cold Spring Harbor, N.Y. (1989).

Thus, the polynucleotide according to the invention, may, e.g., be comprised in a vector which is to be stably transformed/transfected into host microorganism cells. In the vector, the polynucleotide of the invention is under control of an inducible promoter, so that the expression of the gene/polynucleotide can be specifically targeted, and, if desired, the gene or genes may be overexpressed in that way.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above.

In view of the above, the invention also concerns an isolated peptide consisting of an amino acid sequence selected from the group consisting of:

(a) an amino acid sequence shown in one of SEQ ID NOs: 1 to 4;

b) an amino acid sequence of an allelic variant of an amino acid sequence shown in SEQ ID NOs: 1 to 4, wherein said allelic variant is encoded by a nucleic acid molecule that hybridizes under stringent conditions to the opposite strand of a nucleic acid molecule shown in SEQ ID NOs: 5 to 8, respectively;

c) an amino acid sequence of an ortholog of an amino acid sequence shown in SEQ ID NOs: 1 to 4, wherein said ortholog is encoded by a nucleic acid molecule that hybridizes under stringent conditions to the opposite strand of a nucleic acid molecule shown in SEQ ID NOs: 5 to 8; and (d) a fragment of an amino acid sequence shown in SEQ ID NOs: 1 to 4, wherein said fragment comprises at least 10 contiguous amino acids and displays monooxygenase activity.

Also, the invention refers to a host cell/microorganism having been transformed/transfected with the polynucleotide according to the invention or containing a vector as defined above and in particular a microorganism or host cell which is selected from the group consisting of fungi including yeast and bacteria.

It is to be understood that the host microorganism heterologously expresses the newly identified polynucleotide, i.e. at least one of the monooxygenases identified herein, preferably in combination with a protoilludene synthase, or heterologously expresses the gene cluster as set forth further below.

According to another aspect of the invention, a host microorganism is used, with the nucleic acid encoding the polypeptide with monooxygenase activity being adapted to the codon usage of the respective host microorganism.

According to another embodiment of the invention, the host cell is a *Saccharomyces* spp., in particular *Saccharomyces cerevisiae*, an *Aspergillus* spp., in particular *Aspergillus nidulans*, a homobasidiomycete, in particular a homobasidiomycete of the genus *Armillaria*, in particular *Armillaria gallica, Armillaria mellea, Armillaria ostoyae*, and other members of the genus *Armillaria*.

Yet another aspect of the invention concerns a method for producing melleolides comprising the steps of:

a) growing, under suitable nutrient conditions permissive for the production of a hydroxylated protoilludene or sesquiterpenoid protoilludene-type aryl ester, a microorganism as defined claimed above; and b) isolating said hydroxylated protoilludene or said sesquiterpenoid protoilludene-type aryl ester from the host microorganism or the medium of its growth.

According to an aspect of the invention, the hydroxylated protoilludene is selected from 8-alpha-hydroxy-6-protoilludene; 8-alpha, 13-hydroxy-6-protoilludene; and the sesquiterpenoid protoilludene-type aryl ester is selected from melleolide I, armillaridine, melleolide A, melleolide F, melleolide B, melleolide K, armillyl evernitate, armillarin, arnamiol, melleolide J, armillarivin, 10-alpha-hydroxy-melleolide, armillyl orsellinate, melleolide E, 1-O-trifluoroacetyl-melleolide E, melleolide H, 5'-O-methyl-melledonal, melledonal, arnamial, melleolide C, melleolide D, melledonal A, melledonal C, melledonol, dehydroarmillyloresllinate, armillane, armillaridin.

According to yet another aspect, the method comprising the above mentioned steps consist of the following steps:

a) growing, under suitable nutrient conditions, a host microorganism transformed or transfected to comprise a nucleic acid sequence selected from a) SEQ-ID-NOs: 5 to 8 from the enclosed sequence protocol, b) a nucleic acid sequence complementary to SEQ ID NOs: 5 to 8, and c) nucleic acid sequences which hybridize under stringent conditions to the nucleic acid sequences defined in a) and b) or their complementary strands;

b) overexpressing the nucleic acid sequence;

c) thus, enhancing hydroxylated protoilludene or sesquiterpenoid protoilludene-type aryl ester production in the microorganism cell, and d) isolating said hydroxylated protoilludene or sesquiterpenoid protoilludene-type aryl ester from the microorganism or the medium of its growth.

According to an embodiment of the present invention, the invention also relates to a method for producing a hydroxylated protoilludene and/or a sesquiterpenoid protoilludene-type aryl ester, the method comprising the steps of a) providing a host microorganism that has been transformed to at least heterologously express all of the following: i) a protoilludene synthase, and ii) at least one cytochrome-P450-monooxygenase, wherein at least one of (i) or (ii) is foreign to said host microorganism, b) growing, under suitable nutrient conditions permissive for the production of the sesquiterpenoid protoilludene-type aryl esters, the host microorganism provided in step a); thus producing the hydroxylated protoilludene, and, as the case may be, the sesquiterpenoid protoilludene-type aryl ester.

The host microorganism employed in the method according to the invention thus comprises at least two genes, i.e. a protoilludene synthase and at least one, cytochrome-P450-monooxygenases, preferably CYP-Arm1 to 4 of *Armillaria gallica* as identified in the present invention.

Accordingly, the method can further comprise the step c):

c) isolating said hydroxylated protoilludene and/or said sesquiterpenoid protoilludene-type aryl ester from the host microorganism or the medium of its growth.

In addition, in the method according to the invention, in a preferred embodiment, the protoilludene synthase and/or the cytochrome-P450 monooxygenase is a protoilludene synthases and/or a cytochrome-P450 monooxygenase, respectively, from one of the following: *Armillaria* spp., in particular of *Armillaria gallica* and further preferred the CYP-Arm 1, 2, 3 or 4 or CYP-Arm 1 to 4 monooxygenases as identified herein.

Thus, in a refinement of the method of the invention, the cytochrome P450-monooxygenase has an amino acid sequence selected from the group consisting of:

a) an amino acid sequence shown in any of SEQ ID NOs: 1 to 4 of the attached sequence listing;

b) an amino acid sequence of an allelic variant of an amino acid sequence shown in any of SEQ ID NOs: 1 to 4, wherein said allelic variant is encoded by a nucleic acid molecule that hybridizes under stringent conditions to the opposite strand of a nucleic acid molecule shown in SEQ ID NOs: 5 to 8;

c) an amino acid sequence of an ortholog of an amino acid sequence shown in any of SEQ ID NOs: 1 to 4, wherein said ortholog is encoded by a nucleic acid molecule that hybridizes under stringent conditions to the opposite strand of a nucleic acid molecule shown in SEQ ID NOs: 5 to 8; and d) a functional fragment of an amino acid sequence shown in SEQ ID NO: 2, wherein said fragment comprises at least 10 contiguous amino acids, fulfilling the function of a cytochrome P450-monooxygenase.

Also, in a refinement of the method of the invention, in step a) a microorganism is provided that has further been transformed to express a NADPH-cytochrome P450 reductase, preferably a NADPH:cytochrome reductase from *Taxus chinensis*.

This enzyme is introduced in order to improve the reduction of the heterologous cytochrome P450 enzyme in yeast.

According to a refinement of the host microorganism and/or the method according to the invention, the host microorganism provided in step a) is further transformed to express a 2-hydroxy-3-methylglutaryl-CoA (HMG-CoA) reductase.

This enzyme can be introduced in order to increase flux though the mevalonic acid pathway to provide additional farnesyldiphosphate to boost the protoilludene biosynthesis.

It is to be understood that preferably the sesquiterpenoid protoilludene-type aryl ester is selected from melleolides and armillylorsellinates, in particular from mono-hydroxylated protoilludene, in particular 8-hydroxy-6-protoilludene, di-hydroxylated protoilludene, in particular 8, 13 hydroxy-6-protoilludene.

Accordingly, the invention also relates to the hydroxylated protoilludene or the sesquiterpenoid protoilludene-type aryl ester obtained from a method according to the invention.

Further, the present invention also relates to the use of a polynucleotide as identified herein, or of the vector as described herein, for the production of hydroxylated protoilludene and/or sesquiterpenoid protoilludene-type aryl esters.

In addition, the present invention also relates to the use of a gene cluster comprising at least (i) a protoilludene synthase and (ii) at least one cytochrom-P450-monooxygenase for the production of a hydroxylated protoilludene and/or a sesquiterpenoid protoilludene-type aryl ester.

In a preferred embodiment of the use and the method according to the invention, a gene cluster is used that has a nucleotide sequence shown in SEQ ID NO: 9 of the attached sequence listing.

With the disclosed methods and the targeted expression of the protoilludene synthase and cytochrome-P450 monooxygenases it is possible to produce and accumulate hydroxylated protoilludenes or sesquiterpenoid protoilludene-type aryl esters in the host microorganism or in the medium the host microorganism is contained in. It is to be understood that it lies within the skill and knowledge of a person skilled in the art, to supplement the host microorganism cell(s) or host microorganism cell culture with additional and/or essential precursors or other substances, nutrients or metabolites that might be necessary to complete or assist the enhanced hydroxylated protoilludene or sesquiterpenoid protoilludene-type aryl ester production.

Accordingly, the present invention also relates to hydroxylated protoilludenes or sesquiterpenoid protoilludene-type aryl esters obtained by the method as defined above. The thus generated hydroxylated protoilludenes or sesquiterpenoid protoilludene-type aryl esters can be efficiently used as medicaments, e.g., for treating any bacteria-caused infection or disease.

In view of the above, the invention also refers to the use of a polynucleotide, the vector, or the polypeptide as defined above, respectively, for the production of hydroxylated protoilludenes or sesquiterpenoid protoilludene-type aryl esters.

It is to be understood, that the production of hydroxylated protoilludenes or sesquiterpenoid protoilludene-type aryl esters according to the invention can be performed by means of a heterologous or homologous overexpression of the polynucleotide encoding for protoilludene synthase. Systems and methods, as well as the respective suitable host cells will be apparent to those skilled in the art upon reading the teaching of this invention.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

EXAMPLES

FIG. 1 shows a schematic drawing of some representatives of sesquiterpenoid protoilludene type aryl esters, which are produced by member of the genus *Armillaria*. The two types of sesquiterpenoid protoilludene type aryl esters are divided according to the position of the double bond into armillylorsellinates and melleolides (FIG. 1).

Materials & Methods

Strains and Growth Conditions: *Armillaria gallica* strain FU02472 was cultivated as described previously (Engels et al., "Cloning and Characterization of an *Armillaria gallica* cDNA encoding protoilludene synthase, which catalyzes the first committed step in the synthesis of antimicrobial melleolides, J. Biol. Chem. 286:6871-6878 (2011)). Yeast strain *S. cerevisiae* CEN.PK2-1C (MATa, ura3-52, trp1-289, Leu2-3_112, his3 Δ1, MAL2-8$^c$, SUC2) was obtained from EUROSCARF (EUROpean *Saccharomyces Cerevisiae* Archive for Functional analysis) Universität Frankfurt (Frankfurt am Main, Germany) and maintained on SC minimal medium agar (Engels, et al., "Metabolic engineering of taxadiene biosynthesis in yeast as a first step towards TAxol production", Metab. Eng. 10, 201-206 (2008)). Buffered YP medium (2% w/v tryptone, 1% w/v yeast extract and 50 mM MES, pH5.5) was used with 2% w/v Glucose in batch cultivation and 2% w/v galactose in fed-batch fermentation for induction of the Gal1 promoter driven expression. Transformation of *S. cerevisiae* was done by using the lithium acetate method with selection previously described (Engels, et al., 2008).

Genomic DNA Isolation and Library Construction: *Armillaria gallica* genomic DNA was isolated using the cetyltrimethylammonium bromide method (Murray and Thompson, 1980). For the genomic library construction the Lambda DASH II/BamHI vector kit in combination with the Gigapack III Gold packaging extracts were used according to the manufacturer's guidelines (Stratagene, Heidelberg, Germany). For the construction of an *A. gallica* genome walking library the Clontech (Saint-Germain-en-Laye, France) GenomeWalker™ Universal Kit was used according to the manufacturer's protocol.

Library Screening, Genome Walking and Sequencing: Phage plagues were transferred to charged nylon membranes (GE Healthcare) and screened using $^{32}$P labeled nucleic acid probes. For prehybridization and hybridization Roti®Hybrid Quick (Carl Roth, Karlsruhe, Germany) supplemented with 0.1 mg/ml salmon sperm DNA. For the labeling of probes the DecaLabel™DNA Labelling Kit (Fermentats, St. Leon-Rot, Germany; since 2010 Thermo Fisher Scientific) was used. Membranes were membranes were hybridized for 15 h at 65° C. and then washed four times with diluted Roti®Hybrid Quick hybridization buffer (Roti®Hybrid Quick:H$_2$O 1:2 for 30 min 1:5 for 30 min and 1:10 for twice for 10 min). Membranes were then exposed to X-ray film at –80° C. for 4 days. Isolated positive cosmids were then sequence by primer walking. Obtained fragments from the genome walking PCR amplification were subcloned for DNA sequencing in the Zero Blunt® Cloning Kit (Invitrogen, Karlsruhe, Germany).

Heterologous Expression of Cytochrome P450 in Yeast and Functional Testing Via In-Vivo Feeding: All four *A. gallica* cytochrome P450 dependent monooxygenases were cloned via gateway cloning into the galactose inducible yeast expression vector pYES-DEST52 (Invitrogen). For the heterologous expression of the cytochrome P450 monooxygenases the haploid yeast strain CEN.PK2-1C was used.

To improve the reduction of the heterologous cytochrome P450 enzyme in yeast the *Taxus chinensis* NADPH:cytochrome P450 reductase (Jennewein, et al., "Coexpression in yeast of *Taxus* cytochrome P450 reductase with cytochrome P450 oxygenases involved in Taxol biosynthesis" Biotechnol. Bioeng. 89:588-598 (2005)) was cloned into the pCM183 yeast expression vector for heterologous co-expression. For yeast microsomal fraction preparation approx. 5 g (wet weight) of galactose induced recombinant yeast biomass was used for spheroblast preparation. After spheroblast disruption using glass beads the resulting crude extract was cleared by centrifugation and ER membranes were harvested from the supernatant via a 105.000×g ultracentrifugation for three hours. For the functional testing via in-vivo feeding the cloned *A. gallica* cytochrome P450 monooxygenases were heterologously co-expressed with the *T. chinensis* cytochrome P450 monooxygenase. To the galactose induced strains either cold 6-protoilludene or tritium labeled [$^3$H]-6-protoilludene was used. After overnight incubation to the induced yeast cell cultures 1 ml of brine was added and the culture extracted three times with 5 ml of n-pentane. The organic solvent fractions were pooled and concentrated for radio-thin layer chromatography (TLC) or GC/MS analysis.

Fermentation of Recombinant *S. cerevisiae* for the Total Synthesis of Hydroxyl-Protoilludene: For the total biosynthesis of sufficient amounts of hydroxyl-protoilludene for structure elucidation via NMR-analysis the CEN.PK2-1C yeast strains coexpressing the *A. gallica* cytochrome P450 monooxygenases CYP-Arm3 with the *T. chinensis* NADPH:cytochreome P450 reductase were transformed with a truncated version of the yeast HMG-CoA reductase 1 (Dimster-Denk, et al., "Feedback regulation of 3-hydroxy-3-methylglutaryl coenzyme A reductase in *Saccharomyces cererevisiae*", Mol. Biol. Cell 5:655-665 (1994)) cloned pRS315 vector containing a PGK promoter and cyc1 transcription terminator. *A. gallica* protoilludene synthase was cloned into the pRS423 vector (complementing the yeast CEN.PK2-1C histidine auxotrophy) containing a Gal1 promoter and cyc1 transcription terminator (both obtained from the pYES-DEST52 vector).

NMR Spectrometry: All NMR spectra were recorded on a Bruker DRX 500 MHz NMR spectrometer using a 5 mm BBO probe with an z-gradient. Hydroxyprotoilludene samples were dissolved in deuterated-dichloromethane to a final concentration of about 50 mM and were calibrated with respect to the solvent signals at 5.32 ppm and 54.00 ppm, respectively. $^{13}$C-NMR spectrum was acquired by 1000 scans with a 30° pulse and a delay of 2 seconds. The $^{13}$C-DEPT-135 was acquired by 400 scans. All two-dimensional spectra were acquired using BRUKER standard pulse programs. The DQF-COSY and the gs-NOESY spectra were measured with 512 increments with two or four scans per increment, respectively. A mixing time of 600 ms were used for the NOESY spectrum. Heteronuclear correlation were measured by gs-HSQC and gs-HMBC spectra, acquired with 512 increments with four and eight scans per increment, respectively. Both spectra were optimized for $^1$J and $^n$J couplings of 140 Hz and 8 Hz, respectively. Data were processed using TopSpin 1.3 (Bruker Biospin) and MestReNova 8.0 (MestreLab Research) software.

Results

Isolation of biosynthetic gene cluster using phage library screening and genome walking For the isolation of the protoilludene type sesquiterpenoid gene cluster an *Armillaria gallica* genomic DNA phage library was constructed; screening was performed using *A. gallica* protoilludene synthase as a probe. Two of the obtained positive plaques from the second round of screening were used for cosmid DNA isolation. Restriction digestion of the obtained cosmid DNA showed identical fragment patterns which led to the conclusion that both cosmids are identical. The insert of one of the cosmids (cosmid 5.1) was then sequenced by primer walking which revealed a 22,902 kb fragment.

Analysis of the obtained sequence data identified the previously isolated protoilludene synthase genomic sequence and three sequences with high homology to cytochrome P450 dependent monooxygenases of which one seems to be a partial sequence. In addition to the protoilludene synthase and the cytochrome P450 monooxygenases two sequences with unknown functions (marked as hypothetical proteins) and one sequence with high homology to a GMC oxidoreductase were identified in the ~23 kb fragment.

With protoilludene type aryl esters getting oxygenated at up to eight positions, the identification of three similar cytochrome P450 monooxygenases closely associated with the protoilludene synthase provided already a first indication of a potential clustering of the biosynthetic pathway in *A. gallica*.

Next a genome walking library was constructed by ligating DNA adaptor fragments to restriction digested *A. gallica* genomic DNA and by sequencing the obtained PCR fragments the encountered partial cytochrome P450 monooxygenases of the sequence cosmid insert could be completed. Part of the newly identified sequence was then used to screen an additional 1.7×10$^4$ plaque forming units of the genomic phage library. The screening resulted in one clone which also proved positive in a subsequent second screening round. Sequencing of the cosmid insert revealed an *A. gallica* genomic fragment of 16.27 kb containing an additional cytochrome-P450-monooxygenase (named CYP-Arm1) in addition to three putative genes with homology to a DNA repair endonuclease, a transcriptional activator and a reverse transcriptase. A primer walking attempt 3' to the 5.1 cosmid fragment revealed no further genes with potential function in the terpenoid or polyketide biosynthesis.

FIG. 2 shows the scheme of the terpene biosynthesis part of the melleolide gene cluster obtained from genomic DNA library screening with radioactive probes (protoilludene synthase); the cluster contains the protoilludene synthase ("Pro 1"), four cytochrome-P450-monooxygenases, referred to as "CYP-Arm1", "CYP-Arm2", "CYP-Arm3" and "CYP-Arm4", and two hypothetical proteins.

Amplification of the Identified Cytochrome P450 Monooxyganses from A. Gallica cDNA Library The sequencing of the cloned genomic DNA revealed a high degree of intron/exon fragmentations of the encountered four genomic cytochrome P450 monooxygenase sequences. The genomic sequence of cytochrome-P450 CYP-Arm1 which spreads over 2158 bp contains 10 introns, with exons ranging in size from 38 bp to 537 bp. The genomic sequences of CYP-Arm2 and CYP-Arm3 show high similarity, both containing 11 introns and possessing an overall sequence identity of 73.8%. The analysis of CYP-Arm4 identified an open reading frame coding for a 509 amino acid protein, the deduced ORF is interrupted by 14 introns yielding exons of 4 to 190 bps in length. Further analysis of the isolated cytochrome-P450-monooxygenases on amino acid sequence level displays an amino acid sequence similarity of CYP-Arm1, CYP-Arm2 and CYP-Arm 3 compared to CYP-Arm 4 of 32.5%, 34.0% and 34.0%, respectively.

Based on these predicted sequences the corresponding cDNAs were amplified by polymerase chain reaction from an A. gallica cDNA library. Sequencing of several subcloned PCR fragments revealed a significant fraction of the cDNA clones still containing introns. For all four cytochrome P450 monooxygenase however correct cDNA clones were obtained and subcloned for heterologous expression in Saccharomyces cerevisiae. To facilitate the analysis of correct heterologous expression and localization to the yeast endoplasmic reticulum all four cytochrome P450 monooxygenases were histidine tagged at the C-terminus.

Heterologous Expression of Cytochrome P450 Monooxygenases and Functional Examination.

Figure 3:
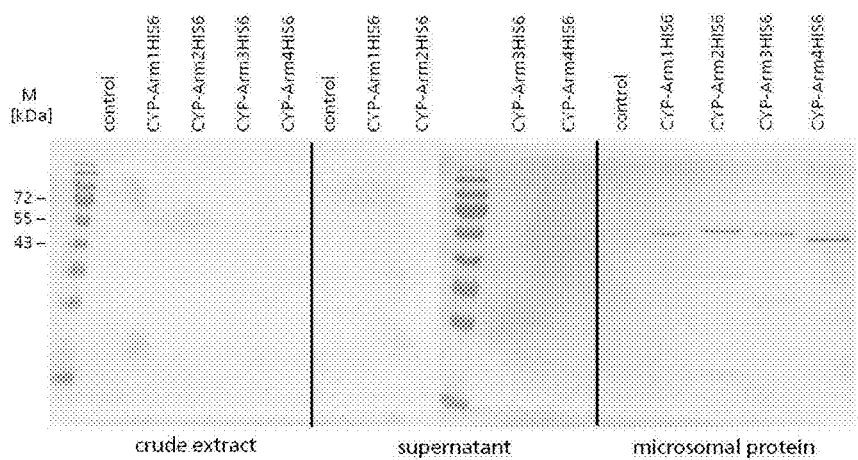
FIG. 3 shows Western Blot results of different samples from microsomal protein preparation of cytochrome-P450-monooxygenase CYP-Arm 1 to 4 expressing *Saccharomyces cerevisiae* clones and the negative control.

For heterologous expression the four constructed expression constructs containing the isolated A. gallica cytochrome P450 monooxygenases were transformed into yeast CEN.PK2-1C. After induction of the heterologous expression with L-galactose the recombinant yeast cells were harvested and correct localization of the heterologous expressed P450 examined via yeast microsomal protein preparation. The immune blotting analysis using a hexa-histidine specific primary antibody showed the correct localization of the heterologous expressed protein (with an expected molecular weight of 57 to 60 kDa) to the microsomal fraction (see FIG. 3).

For functional testing of the cloned cytochrome P450 dependent monooxygenases the Taxus chinensis NADPH:cytochrome P450 reductase was co-expressed in the recombinant yeast. For an initial functional examination of the cloned A. gallica cytochrome P450 an in vivo feeding approach was taken. For the in vivo feeding experiment to an induced 5 ml yeast culture 15.000 cpm of $^3$H-labeled 6-protoilluden were added and the cultures incubated overnight. The organic extracts of the individual yeast cultures were then analyzed via radio-thin-layer-chromatography (radio-TLC). The radio-TLC analysis for CEN.PK2-1C expressing the CYP-Arm3 together with the T. chinensis cytochrome P450 reductase showed a nearly complete conversion of the feed tritium labeled 6-protoilludene to a more polar, putative hydroxylated product. Also with CYP-Arm2 a more polar product was observed, however conversion occurred here to a much lesser extent. Interestingly the re-extraction of the supplied 6-protoilludene from the yeast cell culture using n-pentane proved difficult, however seemed to improve significantly for hydroxylated derivatives.

Figure 4:
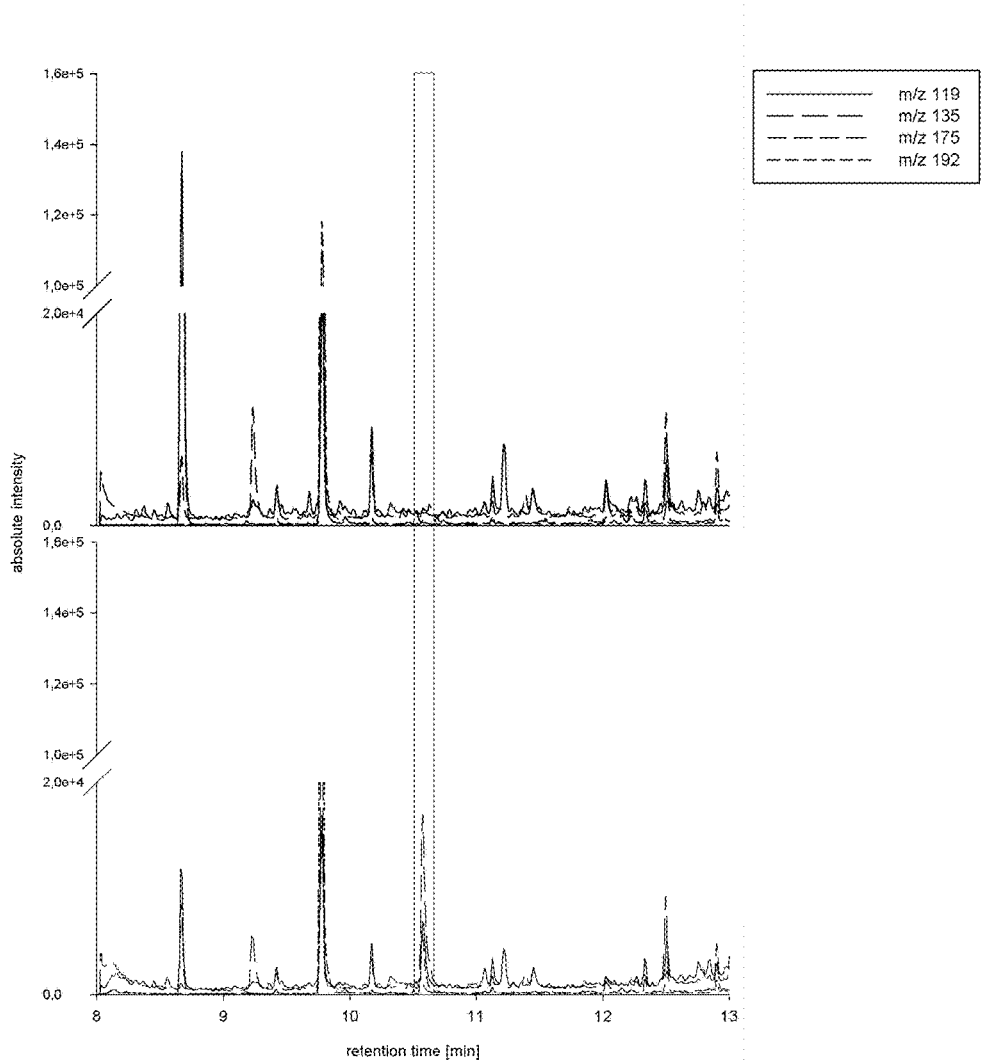
FIG. 4 shows a non-radioactive assay and GC/MS analysis of solvent extract obtained from in-vivo feeding with 6-protoilludene: the extract of in-vivo feeding of the clone expressing CYP-Arm3 reveals an additional peak in contrast to the negative control at retention time 10.6 min.
Figure 5:
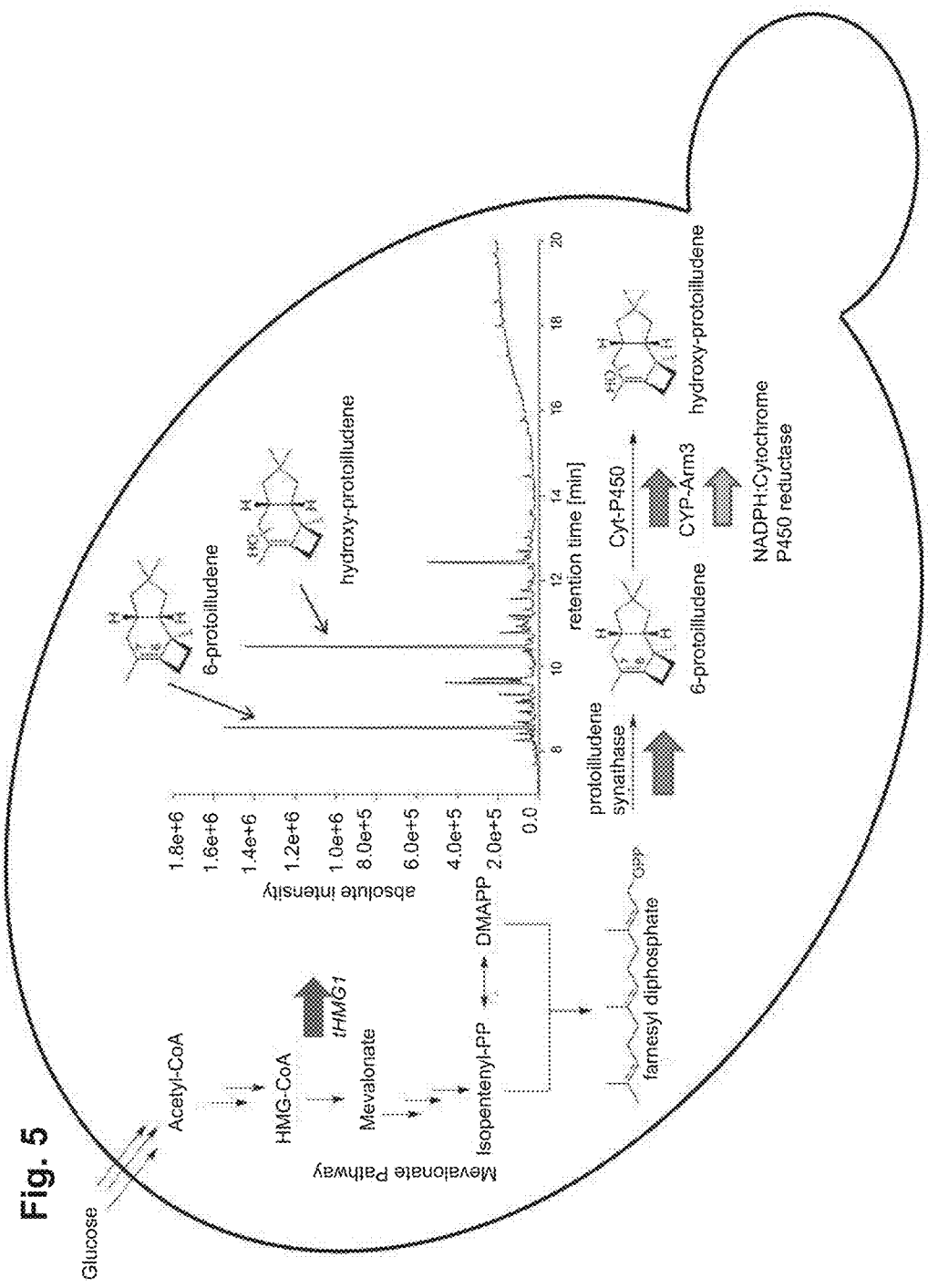
FIG. 5 shows a scheme of budding baker's yeast *Saccharomyces cerevisiae* for production of a putative hydroxy-protoilludene.

For further analysis using GC/MS the recombinant yeast strains were feed with "cold" 6-protoilludene derived from biocatalysis based synthesis reaction using farnesyldiphosphate and recombinant protoilludene synthase. The induced and in vivo feed recombinant yeast cultures were then similarly extracted with n-pentane and the organic extract analysed via GC/MS. The GC-chromatogram of CYP-Arm3 showed in comparison to the negative control (only expressing the T. chinensis NADPH:cytochrome P450 reductase) an additional peak (FIG. 4). The obtained mass spectrum showed masses corresponding to a hydroxyprotoilludene product.

Total Biosynthesis of Hydroxyprotoilludene by Recombinant S. cerevisiae.

Next, the structure of the potential hydroxyprotoilludene product was elucidated via NMR analysis. Since for proper structural elucidation of the compound several milligrams of pure product are required, it was necessary to obtain sufficient material. To this end, and for the purification of the compound to homogeneity and analysis a Saccharomyces cerevisiae strain was engineered capable of total biosynthesis of the putative hydroxyprotoilludene.

Figure 6:
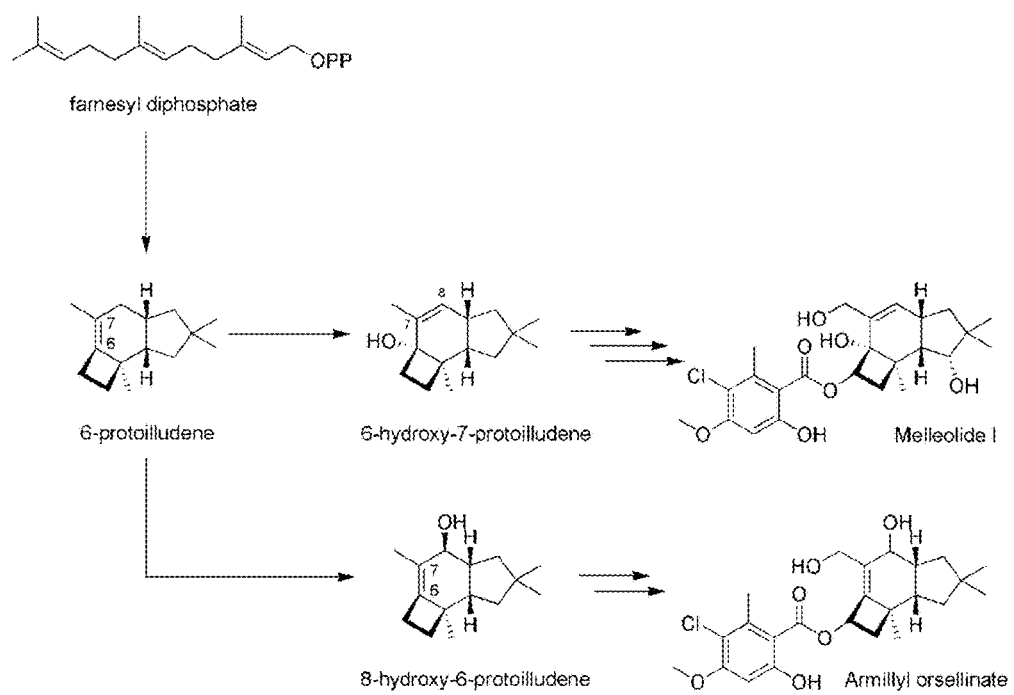
FIG. 6 shows a scheme displaying the structure of hydroxy-protoilludene obtained from fermentation which was elucidated by NMR-spectroscopy as 8-hydroxy-protoilludene.

For the total fermentation the S. cerevisiae CEN.PK2-1C strain transformed with episomal expression vectors containing the T. chinensis NADPH:cytochrome P450 reductase, the cytochrome P450 monooxygenases CYP-Arm3, a truncated version of the yeast HMG-CoA reductase (tHMGR) and the A. gallica protoilludene synthase was employed. The T. chinensis NADPH:cytochrome P450 reductase was heterologously co-expressed in order to increase the reduction and thus catalytic activity of the cytochrome P450 monooxygenase. The truncated, deregulated version of the yeast HMG-CoA reductase was included to increase flux though the mevalonic acid pathway to provide additional farnesyldiphosphate to boost the protoilludene biosynthesis (see FIG. 6).

Table 1 below shows a summary of the transformed plasmids and the heterologously expressed genes in the recombinant S. cerevisiae strain for the production of hydroxyprotoilludene:

TABLE 1

| Plasmid | ORF | Promoter | Auxotrophy |
|---|---|---|---|
| pCM183::P450-Red-tc | cytochrome-P450-reducatse | $P_{cyc1}$ | Tryptophan (TRP1) |
| pRS315::tHMGR-sc | 3-hydroxy-3-methylglutarly-CoA-reductase | $P_{PGK}$ | Leucin (LEU2) |
| pRS423::Pro1HIS6 | protoilludene synthase | $P_{Gal1}$ | Histidine (HIS3) |
| pYES-DEST52::CYP-Arm3HIS6 | cytochrome-P450-monooxygenase CYP-ARM3 | $P_{Gal1}$ | Uracil (URA3) |

Fermentation for total synthesis of the putative hydroxyprotoilludene product using the metabolic engineered strain was carried out on a 2.8 L scale. For the purification of the CYP-Arm3 product the culture supernatant, separated from the biomass, was employed.

Purification of Hydroxyprotoilludene and Structure Elucidation

The obtained culture supernatant was extracted by addition of silica C18 RP powder and incubation at 4° C. for 16 h with constant stirring. The silica C18 RP material was recovered by filtration and dried by lyophilisation. The extraction was performed using a Soxhlet apparatus with n-pentane as organic solvent. The resulting extract was concentrated under vacuum. The crude extract was then purified by chromatography on silica gel 60, chloropropyl-functionalized silica gel and by reverse phase semiprep-HPLC. After three purification steps approximately 40 mg of pure product for NMR analysis could be obtained.

For structural determination both direct $^1$H and $^{13}$C NMR analysis were performed. Table 2 below shows the complete $^1$H- and $^{13}$C-NMR shifts and their assignments as a result of the two dimensional NMR spectra analysis:

TABLE 2

| Number | $^1$H-signals | $^{13}$C-signals |
| --- | --- | --- |
| 1 | 1.35 (dd) | 41.5 (T) |
|   | 1.4 (dd) |   |
| 2 | 2.4 (dt) | 46.7 (D) |
| 3 | — | 45.6 (S) |
| 4 | 1.84 (2H, m) | 36.6 (T) |
| 5 | 2.5 (m) | 25.0 |
|   | 2.7 (m) |   |
| 6 | — | 141.5 (S) |
| 7 | — | 126.8 (S) |
| 8 | 3.98 (d, broad) | 74.5 (D) |
| 9 | 2.2 (m) | 51.1 (D) |
| 10 | 1.16 (t) | 46.9 (T) |
| 11 | — | 40.05 (S) |
| 12 | 1.06 (3H, s) | 20.4 (Q) |
| 13 | 1.64 (3H, s) | 11.1 (Q) |
| 14 | 1.11 (3H, s) | 29.6 (Q) |
| 15 | 0.99 (3H, s) | 22.1 (Q) |
| —OH | 1.47 (broad) | — |

The analysis showed that the isolated compound was 8-hydroxy-6-protoilludene, which is why CYP-Arm 3 has been shown to act as an 8-alpha-hydroxylase. Further, the results showed, for the first time, the functional characterization—together with the elucidation of the molecular structure of the product—of a cytochrom-P450 monooxygenase mediated catalyzation to a sesquiterpene alcohol from a basidiomycete.

In a next step, it was elucidated whether the additional expression of CYP-Arm2 could lead to a di-hydroxylated protoilludene structure.

To this end, the plasmid set to be employed had to be adapted for the expression of a fifth foreign gene. The following table 3 shows the transformed plasmids and the heterologously expressed genes in the recombinant S. cerevisiae strain for the production of di-hydroxylated protoilludene:

TABLE 3

| Plasmid | ORF | Promoter | Auxotrophy |
| --- | --- | --- | --- |
| pCM183::P450-Red-tc | cytochrome-P450-reducatse | $P_{cyc1}$ | Tryptophan (TRP1) |
| pRS315::tHMGR-sc | 3-hydroxy-3-methylglutarly-CoA-reductase | $P_{PGK}$ | Leucin (LEU2) |
| pRS423::Pro1HIS6::CYP-Arm3HIS6 | protoilludene synthase and cytochrome-P450 monooxygenase CYP-Arm3 | 2 × $P_{Gal1}$ | Histidine (HIS3) |
| pYES-DEST52::CYP-Arm2HIS6 | cytochrome-P450-monooxygenase CYP-ARM2 | $P_{Gal1}$ | Uracil (URA3) |

For fermentation of a di-hydroxylated protoilludene, a fermentation was was carried out on a 3 L scale—analogously to the above described fermentation for the production of the mono-hydroxylated 8-alpha-6-protoilludene. For the purification of the product the culture supernatant, separated from the biomass, was subjected to a chloroform extraction. The concentrated extract was analyzed via GC/MS and LC/MS/MS—analogously to the isolation of the 8-alpha-6-protoilludene process.

Purification of Di-Hydroxylated Protoilludene and Structure Elucidation

The obtained culture supernatant was extracted in chloroform-di and air dried, solved in deuterated solvent, and analyzed via GC/MS.

For further structural determination both direct $^1$H and $^{13}$C NMR analysis were performed. Table 4 below shows the complete $^1$H- and $^{13}$C-NMR shifts and their assignments as a result of the two dimensional NMR spectra analysis:

TABLE 4

| Number | $^1$H-signals | $^{13}$C-signals |
| --- | --- | --- |
| 1 | 1.21 (dd) | 41.2 (T) |
|   | 1.32 (dd) |   |
| 2 | 2.32 (dt) | 46.1 (D) |
| 3 | — | 45.6 (S) |
| 4 | 1.78 (2H, m) | 36.1 (T) |
| 5 | 2.58 (m) | 24.8 |
|   | 2.7 (m) |   |
| 6 | — | 141.9 (S) |
| 7 | — | 126.9 (S) |
| 8 | 4.07 (d, broad) | 74.8 (D) |
| 9 | 2.25 (m) | 51.1 (D) |
| 10 | 1.06 (t) | 46.3 (T) |
|   | 1.7 (dd) |   |
| 11 | — | 39.8 (S) |
| 12 | 0.98 (3H, s) | 20.2 (Q) |
| 13 | 4.15 (3H, s) | 59.0 (Q) |
| 14 | 1.02 (3H, s) | 29.5 (Q) |
| 15 | 0.89 (3H, s) | 27.0 (Q) |
| —OH | (broad) | — |

The analysis of the spectra showed that the isolated compound was 8-alpha-13-hydroxy-6-protoilludene. As a consequence, the cytochrome-P450 monooxygenase CYP-Arm2 has been characterized to act as a 13-hydroxylase.

With the described heterologously introduced biosynthesis, for the first time a di-hydroxylated sesquiterpene alcohol has been produced in S. cerevisiae and has been structurally characterized.

The identification of the gene cluster from A. gallica described herein, the identification of other sesquiterpene-biosynthesis pathways in basidiomycetes is possible.

The invention claimed is:

1. A recombinant vector, comprising a nucleic acid sequence encoding a *Armillaria gallica* polypeptide with cytochrome-P450 monooxygenase activity, the nucleic acid sequence being operably linked to control sequences recognized by a host microorganism transformed with the vector, wherein the nucleic acid sequence encodes one of SEQ ID NOs: 1-4.

2. The vector of claim 1, wherein the vector is an expression vector.

3. An isolated host microorganism transformed with the vector of claim 1.

4. The isolated host microorganism of claim 3, wherein the host microorganism is selected from the group consisting of fungi, including yeast, and bacteria.

5. The isolated-host microorganism of claim 3, wherein that the nucleic acid sequence encoding the *Armillaria gallica* polypeptide with cytochrome P450-monooxygenase activity is adapted to the codon usage of the host microorganism.

6. The isolated host microorganism of claim 3, wherein the host microorganism is a *Saccharomyces* spp.

7. The isolated host microorganism of claim 3, wherein the host microorganism is further transformed to comprise a protoilludene synthase.

8. The isolated host microorganism of claim 3, wherein the host microorganism is further transformed to express: (i) a NADPH-cytochrome P450 reductase, in particular a NADPH:cytochrome reductase from *Taxus chinensis*, and/or (ii) a 2-hydroxy-3-methylglutaryl-CoA (HMG-CoA) reductase.

9. The host microorganism of claim 3, wherein the host microorganism is a *Saccharomyces cerevisiae*, an *Escherichia coli* or an *Aspergillus nidulans*.

10. The host microorganism of claim 3, wherein the host microorganism is an *Armillaria* spp.

11. The host microorganism of claim 10, wherein the host microorganism is *Armillaria gallica* or *Armillaria mellea*.

12. An isolated recombinant host microorganism modified to express a cytochrome P450-monooxygenase polypeptide not naturally occurring in the host microorganism, wherein the cytochrome P450-monooxygenase polypeptide comprises an amino acid sequence that is selected from the group consisting of:
   a) the amino acid sequence of one of SEQ ID NOs: 1 to 4; and
   b) an amino acid sequence having at least 95% homology with at least one of SEQ ID NOs: 1 to 4.

13. The isolated host microorganism of claim 12, wherein the host microorganism is a yeast or a bacteria.

14. The isolated-host microorganism of claim 12, wherein that the polynucleotide encoding the polypeptide with cytochrome P450-monooxygenase activity is adapted to the codon usage of the host microorganism.

15. The recombinant vector of claim 1, comprising
   a) one of SEQ ID NOs: 5 to 8; and/or
   b) a nucleic acid sequence fully complementary to one of SEQ ID NOs: 5 to 8.

16. The isolated host microorganism of claim 3, wherein the host microorganism is further transformed to express (i) a NADPH:cytochrome reductase from *Taxus chinensis*, and/or (ii) a 2-hydroxy-3-methylglutaryl-CoA (HMG-CoA) reductase.

17. A method for producing a hydroxylated protoilludene and/or a sesquiterpenoid protoilludene-type aryl ester, the method comprising the steps of
   a) providing a host microorganism that has been transformed with i) a polynucleotide encoding a protoilludene synthase, and ii) the recombinant vector of claim 1, wherein both (i) and (ii) are expressed in the host microorganism; and
   b) growing the host microorganism provided in step a, under suitable nutrient conditions permissive for the production of the sesquiterpenoid protoilludene-type aryl esters),
   thereby producing the hydroxylated protoilludene, and/or the sesquiterpenoid protoilludene-type aryl ester.

18. The method of claim 17, further comprising:
   c) isolating said hydroxylated protoilludene and/or said sesquiterpenoid protoilludene-type aryl ester from the host microorganism or the medium of its growth.

19. The method of claim 17, wherein the protoilludene synthase is an *Armillaria* spp. protoilludene synthase.

20. The method of claim 17, wherein the host microorganism in step a) has been transformed is transformed to express a 2-hydroxy-3-methylglutaryl-CoA (HMG-CoA) reductase.

21. The method of claim 17, wherein the sesquiterpenoid protoilludene-type aryl ester is a melleolide or an armillylorsellinate.

22. The method of claim 17, wherein the hydroxylated protoilludene is a mono-hydroxylated protoilludene, a 8-hydroxy-6-protoilludene, a di-hydroxylated protoilludene, or a 8,13-hydroxy-6-protoilludene.

23. A method for producing hydroxylated protoilludene and/or sesquiterpenoid protoilludene-type aryl esters, wherein in the method comprises:
   expressing the recombinant vector of claim 1 in an isolated host cell, thereby producing the hydroxylated protoilludene and/or sesquiterpenoid protoilludene-type aryl esters.

* * * * *

SEQUENCE LISTING

<160> NUMBER OF SEQ ID NOS: 9

<210> SEQ ID NO 1
<211> LENGTH: 538
<212> TYPE: PRT
<213> ORGANISM: Armillaria gallica

<400> SEQUENCE: 1

```
Met Ala Leu Phe Ser Ala Tyr Ala Leu Ala Phe Ser Leu Leu Met Val
1               5                   10                  15

Pro Leu Ile Leu Tyr Ile Leu Arg Ile Gly Arg Arg Glu Ser Gly Leu
            20                  25                  30

Pro Pro Gly Pro Ser Thr Leu Pro Leu Val Gly Asn Leu His Gln Leu
        35                  40                  45

Pro His Gly Ser Leu His Leu Gln Phe Thr Ala Trp Ala Lys Glu Phe
    50                  55                  60

Gly Gly Ile Phe Ser Leu Lys Phe Gly Pro Gly Thr Val Ile Val Ala
65                  70                  75                  80

Thr Ser Pro Arg Ala Val Arg Glu Leu Ile Asp Gln Lys Ser Ala Ser
                85                  90                  95

Thr Ser Asp Arg Pro Pro Ser His Phe Ser Asn Val Ile Thr Gly Gly
            100                 105                 110

Asn Asn Ile Gly Phe Ala Arg Tyr Ser Asp Tyr Trp Arg Arg Gly Arg
        115                 120                 125

Arg Val Met His Ser Met Leu Thr Lys Lys Ala Cys Val Asn His Leu
    130                 135                 140

Thr Ile Gln Arg Ala Glu Ala Ser Gln Leu Met Tyr Asp Tyr Leu Val
145                 150                 155                 160

Glu Pro Lys Val Asn Leu Ser His Gln Ile Leu Val Ala Asn Val Gly
                165                 170                 175

Lys Ser Asp Val Gln Cys Gln Glu Phe Val Ala His Gly Gln Arg Tyr
            180                 185                 190

Ala Asn Ser Val Ile Thr Ser Ile Leu Ala Gly Thr Arg Ser Pro His
        195                 200                 205

His Thr Ser Pro Leu Val Thr Ala Phe Phe Gln Met Gln His Glu Trp
    210                 215                 220

Thr His Leu Leu Thr Pro Gly Ala His Pro Pro Val Asp Met Val Pro
225                 230                 235                 240

Phe Leu Lys Tyr Ile Pro Gly Ser Trp Lys Gln Ile Cys Ala Lys Met
                245                 250                 255

Lys Val Ser Gln Glu Glu Leu Tyr Gly Gly Met Ile Asp Ala Cys Ala
            260                 265                 270

Lys Arg Val Glu Arg Gly Ile Arg Asn Gly Cys Phe Leu Glu Gly Glu
        275                 280                 285

Leu Glu Asn Lys Asp Val Asp Arg Gly Leu Leu Arg Gly Met Cys Ser
    290                 295                 300

Ala Leu Met Glu Gly Gly Ser Asp Ser Thr Ser Ile Tyr Leu Gln Ser
305                 310                 315                 320

Phe Ile Leu Met Leu Val Ala His Pro Asp Val Gln Ala Lys Ala Arg
                325                 330                 335

Ala Glu Ile Asp Ser Val Val Gly Leu Asp Arg Leu Pro Asp Ile Glu
            340                 345                 350

Asp Met Asp Asn Leu Pro Tyr Val Ser Ala Val Ile Lys Glu Val Leu
        355                 360                 365
```

Arg Leu Arg Pro Ile Thr Ala Leu Gly Ala Pro His Tyr Ser Thr Gln
370                 375                 380

Pro Glu Val Val Asp Gly Tyr Val Ile Pro Lys Asn Ser Met Ile Phe
385                 390                 395                 400

Met Asn Gln Trp Gly Met Leu His Asp Pro Asp Ser Tyr Asp Gln Pro
            405                 410                 415

Glu Ser Phe Met Pro Glu Arg Phe Leu Thr Ser Pro Phe Gly Thr Arg
            420                 425                 430

Pro Gly Ala Asp Asp Thr Gly Arg Ser Lys Asp Ile Tyr Phe Gly Gly
            435                 440                 445

Gly Arg Arg Ile Cys Val Gly Met His Phe Gly Gln Asn Ser Leu Ala
450                 455                 460

Ile Thr Ser Met Tyr Leu Ile Trp Ala Phe Asn Leu Thr Asn Ala Ile
465                 470                 475                 480

Asp Pro Gln Thr Lys Asn Pro Ile Pro Val Asp Ile Asn Glu Tyr Asp
            485                 490                 495

Ile Ser Leu Asn Thr Ile Pro Lys Pro Phe Lys Cys Asp Phe Gln Val
            500                 505                 510

Arg Ser Glu Glu His Lys Arg Met Val Glu Asn Ala Phe Ala Glu Ser
            515                 520                 525

Arg Gln Val Leu Ala Pro Phe Glu Gln Asp
530                 535

<210> SEQ ID NO 2
<211> LENGTH: 513
<212> TYPE: PRT
<213> ORGANISM: Armillaria gallica

<400> SEQUENCE: 2

Met Thr His Ala Ser Ser Ala Trp Phe Leu Ala Ala Val Ala Ile Val
1               5                   10                  15

Thr Phe Ile Val Val Arg Arg Ile Arg Ser Ser Trp Arg Lys Leu Pro
                20                  25                  30

Pro Gly Pro Arg Gly Leu Pro Ile Val Gly Asn Leu Leu Gln Leu Arg
            35                  40                  45

Ser Lys Gln Trp Leu Thr Phe Thr Glu Leu Gly Lys Lys Tyr Gly Asp
50                  55                  60

Leu Met Tyr Phe Asn Val Ala Gly Gln Pro Leu Ile Val Ile Asn Ser
65                  70                  75                  80

Leu Arg Val Ala Thr Asp Leu Leu Asp Arg Ala Lys Phe Ser Asp Arg
                85                  90                  95

Pro Arg Asn Ile Val Ala Ser Asp Ile Met Thr Arg Gly Met Phe Val
            100                 105                 110

Ala Phe Ala Pro Tyr Gly Asn Ala Trp Arg His Met Arg Lys Ala Ala
            115                 120                 125

His Glu Gly Leu Asn Lys Asn Ile Val Asn Gln Tyr His Pro Ile Gln
130                 135                 140

Ile Lys Glu Ala Val Leu Leu Ala Asn Asp Leu Leu Ala Glu Pro Asn
145                 150                 155                 160

Arg Trp Val Ser His Val Arg Arg Thr Ala Ala Ser Thr Ile Met Ser
                165                 170                 175

Ile Val Tyr Asp Lys Pro Ala Thr Ser Glu Gln Asp Pro Ser Ile Lys
            180                 185                 190

Arg Ile Asn Asp Phe Ala Ala Arg Leu Thr Arg Ala Ala Met Pro Gly
            195                 200                 205

```
Ala His Phe Val Glu Ser Phe Pro Trp Met Leu Arg Ile Pro Ser Lys
        210                 215                 220

Tyr Ala Lys Trp Lys Arg Glu Ala Glu Gly Trp Tyr Ala Lys Asp Ser
225                 230                 235                 240

Ser Met Phe Glu Ser Leu Phe His Ser Val Lys Asp Arg Val Ala Glu
                245                 250                 255

Gly Asn Asn Arg Pro Ser Phe Val Ala Thr Leu Ile Gln Gly Ala Gly
                260                 265                 270

Arg His Gly Leu Thr Asp His Glu Ser Ser Trp Leu Ala Gly Ala Met
            275                 280                 285

Tyr Thr Ala Gly Val Glu Ser Ser Ala Ala Ile Ser Trp Trp Met
290                 295                 300

Leu Ala Met Ile Leu Tyr Pro Asp Ala Gln Lys Arg Ala Gln Ala Glu
305                 310                 315                 320

Leu Asp Lys Val Val Gly Arg Asp Arg Leu Pro Ala Phe Ser Asp Tyr
                325                 330                 335

Glu His Leu Pro Tyr Val Arg Ala Met Val Lys Glu Thr Leu Arg Trp
            340                 345                 350

Arg Ala Val Asp Pro Val Gly Leu Pro His Arg Ser Thr Glu Asp Asp
            355                 360                 365

Ile Tyr Asn Gly Tyr Phe Ile Pro Ala Gly Ser Ile Leu Ile Ala Asn
370                 375                 380

Val Trp His Ile Asn Arg Asp Pro Glu Asn Tyr Gly Leu Asp Ala Glu
385                 390                 395                 400

His Phe Asp Pro Ala Arg His Leu Asp Glu Thr Gly Gln Leu Ala Pro
                405                 410                 415

Val Ala Gly Thr Lys Glu Glu Asn His Val Ser Phe Gly Phe Gly Arg
            420                 425                 430

Arg Ile Cys Val Gly Arg His Ile Ala Asn Asp Thr Leu Phe Ala Val
            435                 440                 445

Ile Ala Thr Leu Leu Trp Ala Ile His Ile Glu Pro Ala Thr Asp Glu
450                 455                 460

Lys Gly Ala Ser Leu Pro Leu Asp Val Asp Gly Cys Ile Glu Asp Gly
465                 470                 475                 480

Val Val Val Arg Pro Leu Pro Phe Lys Val Lys Val Thr Pro Arg Phe
                485                 490                 495

Ser Glu Ala Gln Ala Ile Val Glu Gln Glu Arg Glu Leu Leu Gly His
                500                 505                 510

Tyr
```

<210> SEQ ID NO 3
<211> LENGTH: 521
<212> TYPE: PRT
<213> ORGANISM: Armillaria gallica

<400> SEQUENCE: 3

```
Met Thr Arg Ile Phe Ser Glu Glu Val Ser Pro Ile Trp Ile Leu Thr
1               5                   10                  15

Ala Ile Val Val Val Ala Tyr Thr Thr Val Arg Tyr Leu Arg Ser Pro
                20                  25                  30

Trp Arg Asn Leu Pro Pro Gly Pro Arg Gly Leu Pro Leu Ile Gly Asn
            35                  40                  45

Leu Leu Glu Leu Arg Gly Lys Gln Trp Leu Thr Phe Thr Glu Leu Gly
50                  55                  60
```

```
Lys Lys Tyr Gly Asp Leu Met Tyr Phe Asn Val Ala Gly Gln Pro Leu
 65                  70                  75                  80

Val Val Leu Asn Ser Gln Lys Val Ala Ala Asp Leu Leu Asp Arg Arg
                 85                  90                  95

Ala Gly Lys Tyr Ser Asp Arg Pro Arg Asn Ile Val Ala Ser Asp Ile
            100                 105                 110

Met Thr Gly Gly Asn Leu Val Val Phe Thr Arg Tyr Gly Asp Val Trp
        115                 120                 125

Arg Arg Met Arg Lys Ala Ala His Glu Gly Leu Asn Lys Gly Val Val
    130                 135                 140

Tyr Lys Tyr His Pro Ile Gln Thr Ala Glu Ala Val Leu Leu Thr Ala
145                 150                 155                 160

Gly Val Leu Ala Glu Pro Glu Lys Trp Asn Ser His Leu Arg Arg Thr
                165                 170                 175

Ala Ala Ser Ala Ile Met Ser Met Val Tyr Asp Thr Pro Pro Thr Ser
            180                 185                 190

Glu Gln Asp Pro Ser Val Lys Asn Ile Asn Glu Phe Val Ala Arg Leu
        195                 200                 205

Thr Arg Ala Ala Met Pro Gly Ala His Phe Val Glu Phe Pro Trp
210                 215                 220

Met Arg Tyr Ile Pro Ser Lys Tyr Ala Lys Trp Lys Arg Glu Ala Glu
225                 230                 235                 240

Glu Ser Tyr Ala Lys Asp Ser Ala Met Phe Glu Gly Leu Phe Asn Gly
                245                 250                 255

Val Lys Asp Arg Val Ala Lys Gly Asp Glu Arg Pro Ser Leu Ala Ser
            260                 265                 270

Thr Leu Ile Gln Asp Ala Gly Arg His Asp Leu Thr Asp Arg Glu Asn
        275                 280                 285

Ser Trp Leu Ala Gly Thr Met Tyr Ala Ala Gly Ala Glu Thr Thr Ser
    290                 295                 300

Gly Val Met Ser Trp Trp Thr Leu Ala Met Ile Val Tyr Pro Glu Thr
305                 310                 315                 320

Gln Lys Arg Ala Gln Ala Glu Leu Asp Ala Val Val Gly Arg Asp Arg
                325                 330                 335

Leu Pro Ser Phe Ala Asp Tyr Glu His Leu Pro Tyr Ile Arg Ala Met
            340                 345                 350

Val Lys Glu Ala Leu Arg Trp Arg Met Val Asp Pro Val Gly Leu Pro
        355                 360                 365

His Thr Ser Thr Glu Asp Asp Val Tyr Asp Gly Tyr Phe Ile Pro Ala
    370                 375                 380

Gly Thr Ile Ile Ile Ala Asn Val Trp His Leu Asn Arg Asp Pro Glu
385                 390                 395                 400

Ile Tyr Gly Pro Asp Ala Glu His Phe Asn Pro Ala Arg His Leu Asp
                405                 410                 415

Lys Asp Gly Lys Leu Ala Pro Gly Pro Ala Asp Thr Lys Glu Glu Ser
            420                 425                 430

His Val Thr Tyr Gly Phe Gly Arg Arg Ile Cys Val Gly Arg His Val
        435                 440                 445

Ala Asn Asn Ser Leu Phe Ile Asp Ile Ala Met Met Leu Trp Ala Met
    450                 455                 460

Asn Ile Glu Arg Ala Thr Asp Glu Asn Gly Val Pro Leu Pro Leu Asp
465                 470                 475                 480
```

-continued

```
Val Asp Gly Cys Val Glu Asp Gly Leu Val Thr Arg Pro Val Pro Phe
                485                 490                 495

Lys Ala Lys Ile Thr Pro Arg Phe Arg Glu Ala Gln Ala Ile Val Glu
            500                 505                 510

Gln Glu Arg Glu Leu Leu Gly Tyr His
        515                 520

<210> SEQ ID NO 4
<211> LENGTH: 509
<212> TYPE: PRT
<213> ORGANISM: Armillaria gallica

<400> SEQUENCE: 4

Met Asp Ser Ala Ser Leu Ala Val Val Trp Ala Ile Leu Leu Val
1               5                   10                  15

Leu Trp Leu Arg Arg Ile Phe Gly Gln Arg Ser Ser Leu Pro Leu Pro
            20                  25                  30

Pro Ala Pro Pro Gly Tyr Pro Val Ile Gly Asn Leu Leu Asp Leu Ala
            35                  40                  45

Asn Asn Asp Val His Ile Arg Ala Arg His Trp Ser Arg Asn Phe Asp
    50                  55                  60

Asp Val Ile Ser Leu Lys Val Leu Gly Lys Thr Met Ile Ile Leu
65                  70                  75                  80

Asn Ser Pro Thr Ala Val Ser Asp Leu Phe Asp Lys Arg Ala Ser Asn
                85                  90                  95

Tyr Ser Asp Arg Pro Asp Met Pro Met Ile Val Asp Leu Met Gly Trp
            100                 105                 110

Asp Trp Thr Phe Ala Leu Met Arg Tyr Gly Pro Arg Trp Lys Glu His
            115                 120                 125

Arg Arg Val Phe Asn Asn His Phe Asn Ile Gly Thr Ser Gly Ala Ser
            130                 135                 140

Glu Asp Arg His Ile Gln Leu Arg Ile Cys Arg Glu Leu Leu Ser Leu
145                 150                 155                 160

Met Phe Gln Ser Pro Ser Lys Tyr Leu Glu Asn Leu Arg His Tyr Thr
                165                 170                 175

Gly His Ile Ile Leu Lys Arg Thr Tyr Gly His Thr Val Val Asp Glu
            180                 185                 190

Lys Asp Pro Tyr Ile Arg Leu Val Glu Ala Ala Ser Gln Ser Thr Ser
            195                 200                 205

Glu Ala Ala Val Pro Gly Ala Phe Leu Val Asp Leu Phe Pro Ser Met
    210                 215                 220

Lys Tyr Ile Pro Glu Trp Val Pro Gly Ala Gln Phe Lys Arg Lys Ala
225                 230                 235                 240

Arg Glu Trp Arg Lys Leu Ser Glu Ala Met Ile Asn Ala Pro Tyr Asp
                245                 250                 255

Met Ala Lys Gly Lys Phe Asp Glu Gly Asn Ala Glu Pro Cys Phe Val
            260                 265                 270

Ser Ala Cys Leu Glu Gln Asn Lys Thr Ala Ser Gly Gln Gly Leu Ser
            275                 280                 285

Glu Glu Leu Ile Lys Asp Thr Ala Ala Val Ala Tyr Ala Ala Gly Ala
        290                 295                 300

Asp Thr Ser Val Ser Thr Leu Thr Thr Phe Ile Leu Ala Met Thr Leu
305                 310                 315                 320

Tyr Pro Asp Val Gln Lys Ala Ala Gln Ala Glu Leu Asp Ala Leu Leu
                325                 330                 335
```

Gly Gly Glu Arg Leu Pro Asp Phe Gly Asp Lys Thr Arg Leu Pro Tyr
            340                 345                 350

Val Thr Ala Ile Leu Lys Glu Val Leu Arg Trp Ile Pro Val Leu Pro
            355                 360                 365

Met Ala Val Pro His Arg Ala Val Asn Ala Asp Thr Tyr Lys Gly Tyr
            370                 375                 380

Tyr Ile Pro Ala Gly Ala Phe Val Tyr Gly Asn Ala Trp Ala Ile Leu
385                 390                 395                 400

His Asn Pro Asp Ile Phe Ala Asp Pro Glu Thr Phe Arg Pro Asp Arg
                405                 410                 415

Phe Ile Glu Asn Pro Thr Leu Leu Asn Pro Ile Asp Asn Gly Val Phe
            420                 425                 430

Gly Phe Gly Arg Arg Ala Cys Ala Gly Arg Val Met Ala Leu Asp Thr
            435                 440                 445

Met Trp Ile Ala Met Ala Ser Ile Leu Ala Val Phe Asp Ile Ser Lys
            450                 455                 460

Ala Val Asp Glu Arg Gly Asn Glu Ile Ser Pro Val Lys Leu Ser
465                 470                 475                 480

Pro Gly Thr Ile Ser His Pro Ala Pro Phe Pro Cys Ile Ile Lys Pro
            485                 490                 495

Arg Ser Lys Ala Ala Leu Glu Leu Ile Thr Gln Asp Asp
            500                 505

<210> SEQ ID NO 5
<211> LENGTH: 1617
<212> TYPE: DNA
<213> ORGANISM: Armillaria gallica

<400> SEQUENCE: 5
atggccctct ctcagcata tgctctcgcg ttctcacttt tgatggtccc cttgatcctc      60
tacatactta ggatcgggag aagggagagt gggcttcccc cagggccgtc tacgctaccc     120
ttggtaggta acctccacca gctcccacac ggtagtctgc atctacaatt cactgcctgg     180
gcgaaggaat cggagggat cttctcgctg aaatttggtc ccggaacggt cattgtcgcg      240
acgagccctc gcgccgttcg tgagctaatt gatcagaaga gtgcaagcac ctcagatcgt     300
ccaccgtcac acttttcgaa tgtcatcacc ggcgggaaca acattgggtt tgctcgctac     360
tcggactact ggcgacgagg acgtcgtgtc atgcactcga tgctcacgaa gaaggcgtgc     420
gtaaatcatc tgactatcca acgcgccgaa gcttcgcagt tgatgtacga ctaccttgtc     480
gagcctaagg tgaacctctc ccatcaaatc ctagttgcaa acgtgggaa atctgacgtt      540 caatgtcagg aattcgtcgc ccatggtcag cgttacgcca attcggtgat cacttcaatc     600
cttgctggta cccggtcgcc gcaccatacc agcccgctcg tcaccgcttt cttccaaatg     660
cagcatgaat ggactcacct cctcacgcct ggcgcccacc ccctgtcga tatggtgccc      720 ttcttgaaat acatcccagg aagttggaag caaatttgcg ccaaaatgaa ggtctcccag     780
gaggagctat acgtgggat gatcgatgcc tgcgcaaagc gcgtcgaacg cggtatacgc      840
aatggatgct ttttggaagg tgagctagag aacaaggatg tggaccgtgg attgctacga     900
gggatgtgtt ccgcgctcat ggaggcgga tcggattcga cgtctatata tttgcagagc     960
ttcattctta tgcttgtagc gcacccagat gtccaagcaa aggctcgcgc agagatagac    1020
tcggtcgtcg gactggatcg attgcctgac attgaagata tggacaatct tccctatgtg    1080
tcagccgtaa ttaaagaggt actgcgtctt cgacctatca cagcgctggg agcaccacat    1140

```
tatagtaccc agcctgaagt tgttgacggc tacgtgattc caaagaactc gatgatcttc    1200
atgaatcaat ggggcatgct acacgaccca gactcctatg accaaccaga atcattcatg    1260
cccgagcgct tcctgacatc gccatttggc acaaggcctg gagcggatga tacgggccgg    1320
agtaaagata tttacttcgg tggcgggagg cgcatctgtg ttggcatgca tttcggacag    1380
aactcgctag ccattacgag catgtatctt atttgggcgt tcaacttgac caatgctatc    1440
gacccacaga ccaagaaccc aatccctgtg gatatcaatg aatatgacat cagcctcaat    1500
acgataccga aaccttcaa gtgcgacttc caagtgagga gtgaagaaca caaacgcatg    1560
gtcgagaatg cgtttgcaga atcgcgccag gttttggcgc catttgagca ggattag     1617
```

<210> SEQ ID NO 6
<211> LENGTH: 1542
<212> TYPE: DNA
<213> ORGANISM: Armillaria gallica

<400> SEQUENCE: 6

```
atgacacacg catcgtctgc ttggtttctg gctgctgtgg ctatcgtcac cttcatcgtc     60
gttcgtcgca tccgtagctc ttggcgcaag ctcccacctg gacctagagg ccttcctatc    120
gttggcaatc ttctccagct acgtagcaaa caatggctca catttaccga gctgggaaag    180
aaatatggcg accttatgta cttcaatgtc gccggacagc ctctcatagt catcaactcc    240
ctgagggttg ccacagatct cttagatcgt gcaaagtttt cggaccgccc acgcaacatc    300
gtcgcctcag acataatgac tagaggcatg ttcgtcgcgt tcgctcctta tgggaatgcc    360
tggcgccata tgcgtaaagc agctcatgaa ggtctcaaca aaaacatcgt gaaccaatac    420
catccaatcc aaatcaagga agctgtcctt cttgcaaacg atttgctggc ggaacccaac    480
cgatgggtat cgcacgttcg ccgtaccgcc gcttctacta tcatgtccat cgtatacgat    540
aagcctgcaa cgtccgaaca agacccatca atcaagcgca tcaacgactt tgctgcacgg    600
ttaacccgtg ctgctatgcc tggtgctcac tttgtggagt cttttccctg gatgctgcgt    660
atccccagca aatacgcaaa gtggaaaagg gaggcagaag gctggtatgc caaagattcg    720
tccatgtttg aaagcctctt ccacagcgtc aaggatcgag tagccgaagg taataatcgt    780
cccagcttcg tggctactct gattcaaggc gccggaagac atgggctgac tgaccatgaa    840
agctcttggc tggcagggc catgtacacg gctggtgtcg aatcgagctc agccgctata    900
tcttggtgga tgcttgctat gatcctttac cctgatgcgc agaaacgagc ccaagcagaa    960
ctcgataagg ttgtcggtcg agatcgactc cccgctttct cagactatga gcatttaccg   1020
tatgttcgtg caatggttaa ggagactctc agatggcgtg cagtggatcc agttgggctc   1080
cctcatcggt cgaccgagga cgatatctat aacggatact cattcccgc cggtagtatc   1140 ctcatcgcca atgtttggca tattaacaga gacccagaga attatggact tgacgccgaa   1200
cacttcgatc cggcccggca ccttgacgag acaggccaac tcgctccggt cgcgggcact   1260
aaggaagaga accacgtttc cttcggtttt ggtcggcgta tctgcgttgg acgacatatt   1320
gctaatgaca ctctgtttgc tgtcatagcc acgttgcttt gggctataca catcgaaccc   1380
gccacggacg agaagggcgc ttcccttccg ttagatgttg acggatgtat tgaagatgga   1440
gtggtcgttc gcccgttacc cttcaaagtc aaggtaactc caaggttttc ggaagcacag   1500
gccattgtgg agcaagagcg ggagcttctt ggccactact aa                      1542
```

<210> SEQ ID NO 7

<211> LENGTH: 1566
<212> TYPE: DNA
<213> ORGANISM: Armillaria gallica

<400> SEQUENCE: 7

| | | | | | |
|---|---|---|---|---|---|
| atgactcgga | tattctcaga | ggaggtgtcg | ccgatatgga | ttttgactgc | aatcgtagtc | 60 |
| gtcgcctaca | ccaccgttcg | ctaccttcgc | agcccttggc | gtaacctccc | cccgggacca | 120 |
| agaggccttc | ctctcatcgg | aaaccttttg | gaacttcgtg | gcaagcaatg | gctcacgttt | 180 |
| actgagctag | ggaaaaaata | tggcgatctc | atgtacttca | atgtcgccgg | gcagccgctg | 240 |
| gtggtcctca | actcccagaa | ggtggcagcc | gacctgcttg | accgtcgcgc | tggaaagtac | 300 |
| tccgaccgcc | cacgcaacat | tgtcgcgtcc | gacatcatga | ctggaggaaa | cttagtcgta | 360 |
| ttcacccgct | atggggatgt | ctggcgccga | atgcgcaagg | cggctcacga | aggtctcaac | 420 |
| aagggtgtcg | tatacaaata | tcatcccatt | cagactgcgg | aagccgttct | tcttacggct | 480 |
| ggcgtgctcg | cggagcccga | aaatggaat | tcacatcttc | gtcgcaccgc | cgcatctgcc | 540 |
| atcatgtcca | tggtatacga | tacgcctcca | acttcagaac | aagatccatc | agtcaagaac | 600 |
| attaatgaat | tgtgtggcacg | attaactcgc | gctgctatgc | caggcgccca | cttcgtggaa | 660 |
| ttcttcccctt | ggatgcggta | catccctagc | aagtacgcaa | agtggaagcg | tgaggcagaa | 720 |
| gaatcatacg | ctaaagattc | tgcgatgttt | gaagggctct | tcaacggtgt | caaggatcgc | 780 |
| gtagccaagg | gtgacgagcg | tcccagtttg | gcgagtactc | tgattcagga | cgcgggaaga | 840 |
| cacgatttaa | ctgacagaga | aaattcgtgg | ctggccggga | ccatgtatgc | tgcgggtgct | 900 |
| gagaccactt | caggtgttat | gtcctggtgg | actcttgcaa | tgattgtcta | ccccgaaaca | 960 |
| cagaaacgag | cacaagcaga | actcgatgct | gtcgttggtc | gcgatcgttt | gccgtctttc | 1020 |
| gccgactatg | aacatttgcc | atacattcgt | gcaatggtca | aggaggccct | caggtggcgc | 1080 |
| atggttgacc | cagtcgggct | tcctcataca | tcgacagaag | acgatgtata | tgacggatac | 1140 |
| ttcatacctg | ccgtaccat | catcatcgcc | aacgtctggc | acctcaacag | agacccagag | 1200 |
| atctatgggc | ccgatgccga | acatttcaac | cctgcccggc | acctcgacaa | ggacggcaag | 1260 |
| ctggcccctg | gacccgcaga | cacgaaggag | gagagtcacg | tcacctacgg | atttgggcga | 1320 |
| cggatttgtg | tgggacggca | cgttgcaaac | aactcttttgt | tcattgacat | agcaatgatg | 1380 |
| ctttgggcta | tgaacatcga | acgtgctacc | gacgagaatg | gtgttcccct | cccgttggat | 1440 |
| gttgacggat | gcgttgaaga | tggactagtc | actcgtccag | tcccttttcaa | ggccaagata | 1500 |
| actccaaggt | tccgggaagc | tcaggcaata | gtagaacaag | agcgagaact | ccttggatat | 1560 |
| cactga | | | | | 1566 |

<210> SEQ ID NO 8
<211> LENGTH: 1530
<212> TYPE: DNA
<213> ORGANISM: Armillaria gallica

<400> SEQUENCE: 8

| | | | | | |
|---|---|---|---|---|---|
| atggattctg | cgtctcttgc | cgttgtcgtt | tgggctatcc | ttctcgtttt | gtggctcaga | 60 |
| aggattttcg | gtcaacgctc | ttccctcccct | ctcccccctg | cacctcctgg | ttatcccgtt | 120 |
| ataggcaacc | tgcttgactt | ggctaacaat | gacgtgcata | tcagagccag | gcactggtcc | 180 |
| cgcaattttg | atgacgatgt | catctctctc | aaagttctgg | gaaagaccat | gataatcttg | 240 |
| aactcgccca | ccgcagtctc | tgatctcttt | gacaagcgag | cctctaacta | ctcagatcgg | 300 |
| cctgacatgc | caatgattgt | tgacttgatg | ggatgggact | ggacatttgc | cctcatgcgg | 360 |

```
tacgggccgc gttggaagga acacagacgg gtcttcaaca accacttcaa tattggcact    420
tctggtgcgt cagaagaccg gcatattcag ctacgcatct gtcgcgagct cttgtccttg    480
atgttccaat ctccttcgaa ataccttgag aaccttcggc actacacagg tcatattatt    540
ctcaaacgca cgtatggaca cacggtagtc gatgagaagg acccttatat ccgcctggtt    600
gaggcagcgt cccaaagtac atctgaagcc gcagtcccag gagccttcct tgtcgatcta    660
ttcccatcga tgaagtatat tcctgagtgg gtcccgggcg cgcaattcaa gagaaaggct    720
agggagtggc gcaaactctc agaagctatg atcaacgcac cgtatgacat ggcgaagggg    780
aaatttgatg aaggaaatgc cgaaccttgc tttgtctctg cttgtctcga gcagaacaag    840
accgcttccg gtcaagggtt gagcgaagaa ctcattaaag acaccgctgc cgtcgcatat    900
gctgccggtg ctgatacgag cgtctccact ctaacgacat ttattctcgc catgacactt    960
tatcccgatg ttcagaaagc agcacaagcc gaactcgatg cattacttgg cggcgaacgt   1020
ttacccgatt ttggcgataa aactcggctg ccatacgtca ctgcaatatt aaaggaggtc   1080
cttcggtgga ttcctgtttt accgatggcc gtacctcacc gagccgttaa tgcggacact   1140
tacaaaggat actacatccc ggctggtgcc ttcgtgtacg gaaacgcatg gctatccttt   1200
cataaccccg acatctttgc agaccccgag acattcagac cagacagatt catcgagaac   1260
ccaacgttac tcaacccgat agacaatggg gtatttgggt ttggaagacg cgcgtgtgca   1320
gggagggtaa tggcgcttga caccatgtgg atagccatgg catccattct agccgtcttc   1380
gacatttcga aagccgtcga tgaacgcggg aatgagatct cacctcccgt aaagctcagt   1440
ccgggaacga taagtcaccc ggcaccattt ccgtgtatta tcaaacctcg atctaaggct   1500
gcccttgaac tcattacgca ggatgactga                                    1530

<210> SEQ ID NO 9
<211> LENGTH: 22204
<212> TYPE: DNA
<213> ORGANISM: Armillaria gallica
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (1520)..(1520)
<223> OTHER INFORMATION: n is a, c, g, or t
<220> FEATURE:
<221> NAME/KEY: misc_feature
<222> LOCATION: (1551)..(1551)
<223> OTHER INFORMATION: n is a, c, g, or t
<220> FEATURE:
<221> NAME/KEY: misc_feature
<222> LOCATION: (1554)..(1554)
<223> OTHER INFORMATION: n is a, c, g, or t
<220> FEATURE:
<221> NAME/KEY: misc_feature
<222> LOCATION: (8100)..(8100)
<223> OTHER INFORMATION: n is a, c, g, or t
<220> FEATURE:
<221> NAME/KEY: misc_feature
<222> LOCATION: (8105)..(8106)
<223> OTHER INFORMATION: n is a, c, g, or t
<220> FEATURE:
<221> NAME/KEY: misc_feature
<222> LOCATION: (8980)..(8980)
<223> OTHER INFORMATION: n is a, c, g, or t
<220> FEATURE:
```

```
<221> NAME/KEY: misc_feature
<222> LOCATION: (8982)..(8982)
<223> OTHER INFORMATION: n is a, c, g, or t
<220> FEATURE:
<221> NAME/KEY: misc_feature
<222> LOCATION: (9701)..(9701)
<223> OTHER INFORMATION: n is a, c, g, or t
<220> FEATURE:
<221> NAME/KEY: misc_feature
<222> LOCATION: (9703)..(9703)
<223> OTHER INFORMATION: n is a, c, g, or t
<220> FEATURE:
<221> NAME/KEY: misc_feature
<222> LOCATION: (10603)..(10603)
<223> OTHER INFORMATION: n is a, c, g, or t
<220> FEATURE:
<221> NAME/KEY: misc_feature
<222> LOCATION: (11508)..(11508)
<223> OTHER INFORMATION: n is a, c, g, or t
<220> FEATURE:
<221> NAME/KEY: misc_feature
<222> LOCATION: (13489)..(13489)
<223> OTHER INFORMATION: n is a, c, g, or t
<220> FEATURE:
<221> NAME/KEY: misc_feature
<222> LOCATION: (14372)..(14372)
<223> OTHER INFORMATION: n is a, c, g, or t
<220> FEATURE:
<221> NAME/KEY: misc_feature
<222> LOCATION: (14396)..(14396)
<223> OTHER INFORMATION: n is a, c, g, or t
<220> FEATURE:
<221> NAME/KEY: misc_feature
<222> LOCATION: (14431)..(14431)
<223> OTHER INFORMATION: n is a, c, g, or t
<220> FEATURE:
<221> NAME/KEY: misc_feature
<222> LOCATION: (14474)..(14474)
<223> OTHER INFORMATION: n is a, c, g, or t
<220> FEATURE:
<221> NAME/KEY: misc_feature
<222> LOCATION: (14484)..(14484)
<223> OTHER INFORMATION: n is a, c, g, or t
<220> FEATURE:
<221> NAME/KEY: misc_feature
<222> LOCATION: (18683)..(18683)
<223> OTHER INFORMATION: n is a, c, g, or t
<220> FEATURE:
<221> NAME/KEY: misc_feature
<222> LOCATION: (19415)..(19416)
<223> OTHER INFORMATION: n is a, c, g, or t
<220> FEATURE:
<221> NAME/KEY: misc_feature
<222> LOCATION: (19480)..(19480)
<223> OTHER INFORMATION: n is a, c, g, or t
<220> FEATURE:
<221> NAME/KEY: misc_feature
<222> LOCATION: (19619)..(19619)
<223> OTHER INFORMATION: n is a, c, g, or t
<220> FEATURE:
<221> NAME/KEY: misc_feature
<222> LOCATION: (19723)..(19723)
<223> OTHER INFORMATION: n is a, c, g, or t

<400> SEQUENCE: 9
atggccctct tctcagcata tgctctcgcg ttctcacttt tgatggtccc cttgatcctc      60
tacatactta ggatcgggag aagggagagt gggcttcccc cagggccgtc tacgctaccc     120
ttggtaggta acctccacca gctcccacac ggtagtctgc atctacantg agtggtggca     180
agatgtccca attctcccct gaacatgtcc tgatngattc actgcctggg cgaaggaatt     240
cggagggatc ttctcggtaa gaactatgaa actcgtcgta aattgtactc atattctaaa     300
tctacgccag ctgaaatttg gtcccggaac ggtcattgtc gcgacgagcc ctcgcgccgt     360
tcgtgagcta attgatcaga agagtgcaag cacctcagat cgtccaccgt cacactttc      420
```

```
gaatgtcatc accggcggga acaacattgg gtttgctcgc tactgtgcgc tcttctctat    480
ttcgtcattt tctattgtcg gctaaatctc ggttcacagc ggactactgg cgacgaggac    540
gtcgtgtcat gcactcgatg ctcacgaaga aggcgtgcgt aaatcatctg actatccaac    600
gcgccgaagc ttcgcagttg atgtacgact accttgtcga gcctaaggtg aacctctccc    660
atcaaatcct agttgcaaac gtggggaaat ctgacgttca atgtcaggaa ttcgtcgccc    720
atggtcagcg ttacgccaat tcggtgatca cttcaatcct tgctggtacc cggtcgccgc    780
accataccag cccgctcgtc accgctttct tccaaatgca gcatgaatgg actcacctcc    840
tcacgcctgg cgcccacccc cctgtcgata tggtgcccct cttgaaatac atcccaggaa    900
gttggaagca aatttgcgcc aaaatgaagg tctcccagga ggagctatac ggtgggatga    960
tcgatgcctg cgcaaagcgc gtcgaacgcg gtatacgcaa tggatgcttt ttggaaggtg   1020
agctagagaa caaggatgtg gaccgtggat tgctacggta tgtcttaaca gtacgcgtgc   1080
cccattttac aaatttatat tttacagagg atgtgttcc gcgctcatgg agggcggatc    1140
ggattcgacg tctatatatt tgcagagctt cattcttatg cttgtagcgc acccagatgt   1200
ccaagcaaag gctcgcgcag agatagactc ggtcgtcgga ctggatcgat tgcctgacat   1260
tgaagatatg gacaatcttc cctatgtgtc agccgtaatt aaagaggtaa gctcttcgct   1320
tcgcctttgt tctatgccag tgtgttcatt acgtatatca taggtactgc gtcttcgacc   1380
tatcacagcg ctgggagcac cacattatag tacccagcct gaagttgtgc gtcattctat   1440
ttttaccttc cgacaattca caaagtgatg tttgctcact tcaggttgac ggctacgtga   1500
ttccaaagaa ctcgatgatn ttcatgaatc aatgtacgta cggtactttc ntcntaccgt   1560
tgcgaactaa agctcccatc ttattgcagg gggcatgcta cacgacccag actcctatga   1620
ccaaccagaa tcattcatgc ccgagcgctt cctgacatcg ccatttggca caaggcctgg   1680
agcggatgat acgggccgga gtaaagatat ttacttcggt ggcgggaggg taagcagcat   1740
gcttgtttat gtacatcggg gtcgtctaac ttttttctaag cgcatctgtg ttggcatgca   1800
tttcggacag aactcgctag taggtttaat ttaacgttgc gatatgccat tacgcatgct   1860
cactgggacg aaaataggcc attacgagca tgtatcttat ttgggcgttc aacttgacca   1920
atgctatcga cccacagacc aagaacccaa tccctgtgga tatcaatgaa tatgacatcg   1980
tgcgtgttgt ctcttatgcg aagtttaccc gtaccttgac aaaagtttcc agagcctcaa   2040
tacgataccg aaacctttca agtgcgactt ccaagtgagg agtgaagaac acaaacgcat   2100
ggtcgagaat gcgtttgcag aatcgcgcca ggttttggcg ccatttgagc aggattagag   2160
gaacatggct tgaaggaaaa tttggttagt gtctacgctg cgacgtcatt cccattaaac   2220
ttagtgagtt taccagctag aataacagta tacagtatac cacatatcac cttagaattt   2280
tgtattacaa ttgctccatc tgcacgggta tgtacgagag aagggttatc agaatatttc   2340
ttcatattgc agtggaccac ctgcgtgact caactttgaa gacacattat cagctcggta   2400
tactaagcgg gggccgaagc aaatcctatg cctaccttat ttttgccatc ggccggactc   2460
tggaaaataa cgttagaatt tcgaactcaa caggccgatt tgtagtggta gccgaagatg   2520
tctgcgttcc tgttcccatt gaaccaggga aggatcgatc gaaatgtcct tgaaacactc   2580
ggtcggtgat gcgcgggcac ccgaacctga agagcacaac ttctcgctac ccgtttggcc   2640
atcggggagc ccacgcaagt ttgaagttgc agattacccg taatagaccg tagcccgaca   2700
agcgcgcccc gaagtgatca agtggaaagt actgattgcg acactagcag ggtcatttgt   2760
```

```
ggagctgaaa ccgaggtgga tttctgaaaa gaaaaagaaa accctagatt accattgcta    2820
acggaagttt cagtcttgca tctaaaaaca agggaacctg ttccattgtt ggtggggcca    2880 tattttttgga aagcgcaaca ctgggcgttt ggcattgcgc gtggatagtc aaacttcaac    2940
acagtaagca tgcggctgtg taagttacgt cgtgacgcat atgcgacctt gctattcgat    3000
tgtatcaatt ctattactat aaaccgttgc ttgcagtgat agcggaagca aatccgagcc    3060
ttcgggtgat cggtatcagg tattgccaat ctcgatgatt tggacctatt gtaagcgcat    3120
ccggcaataa gtaccctcgc acagatgaaa attcaataaa gtttacctca accgggtact    3180
ccagcctcca ggtcttggct catgtccggt gcctgtggag aggctatgtc ccgatttgta    3240
catagcacat acatacgcat cagccaatta tgattcaata tggcttaggc agttcgttcc    3300
cacgtcgata tatcaggcaa cgcttcaaca cgataataat aataaaagcc ccgcgacgcg    3360
tctcgctcga ggcttgttgc tgtgtggcat gtgccaatac tctattatgt cactttaaac    3420
tttcaacctg attatatcag ggcttgtggc catggggatg ctcgtgctgc acggcaaaaa    3480
tcagcgggag cctggcttga tcctaatttc tgtcgcttat gaacatttga agtttgaacc    3540
ctcagcccaa gacgcaaacg gaaaatttgc catcaagtac aaagttgttt gcatctgaaa    3600
tgtactaata catgggcctt caagcaattt tggcactttg agaagcctga aacggtaaga    3660
gcacggtatg cttattttt ttttacttcc ttcgtgcttt ctcgagccgc tgcgcaatcc    3720
tgccaggata cacaagtaag tgtgtccaac acaaacgaca tcgctccgaa aatagtagca    3780
ataatgttac gggtacagag tctccgcctt atagcgtcta gagcaagtga gtcgtgacat    3840
agtattatat gcattctgct ctgtctaact tcccagacta cacctttga caatgatca    3900 aagagaccga ctggagcgta aatacgacct tcaagatact tcaactattg ccaacagatc    3960
atcaaagtta tgcgatgggt ccattgattt tacaagcttg aaaaaggaa ggtggcagaa    4020 gaagtgctgc tgtgcctggt gtcgaggcat ctcgtactct ctcatggacc ggtaaagcaa    4080
cgtcatgtat atctgaccat ccctaaacct acccgttgcc aaagcaaaca attatgactg    4140
tgataaccac tgacaattgc tgcaaagcca tttcatagcc atggtactaa tacttgcttg    4200
tgcttaacaa tactgagcat ggtgcagtac tttcaatgcc tggttttctt gttcaaagtg    4260
actggaatct ccccggagcc ctagcaaatg cgacgcgata gaaagaaaaa gaagactgac    4320
cagaggaggg ttcccggttc gaacggccga ctgataaaat atacataca aatttaggca    4380 aactaaccgc taaaccaagc aagctcaaca catcaccagc acatgctccc tacggtcgca    4440
tccacttgaa aacttgaaaa cttgaattct ccacagacat aacacgtaag cccaggtctt    4500
tgggctttga ggaaagatgt tataatagag cacagtgatg gtcatataca aagacaccga    4560
gttgatatca gctatcgcca ggctgatcat gtcggcaggt ccttacaaaa agagtcaaga    4620
ccgccagcag ccagtcatcc cctcatttga ccctagttgt cgcccgtaac acttggtcta    4680
taggaggtcg cagcccgcca cttcataacc ctagattctc tgatcttcaa tgccttgcct    4740
tgagacgtag ttgcgacaac cctcatcgac ggcatgctat cggtgaattg gtctagcaag    4800
aaagtggctt ttatcatacg tatttctccc gagttgctca gcgtactgga gaactgtaaa    4860
ttgaagattt ccaggctgtc gtcacagcgc cccagtatca tccagcgtgg gtcgcttcct    4920
cagccccacc tcttgacgta tactttcatt acatatgaag aactcctgcg tggaaagcaa    4980
gggtcctgaa ttggctgata ctttacttcc ttacatgaaa gtatatcaca cactgagaag    5040
ataaaatttt actgaatcat ttcccttag tagtggccaa gaagctcccg ctcttgctcc    5100
acaatggcct gtgcttccga gaaccttgga gttaccttga ctttgaaggg taacgggcga    5160
```

```
ctgcaaggca tacgatcaat aaatgtcgta cgtaatggcg aacgagaact acgcacacga    5220
ccactccatc ttcaatacat ccgtcaacat ctaacggaag ggaagcgccc ttctcgtccg    5280
tggcgggttc gatgtgtata gcccaaagca acgtggctat gacagcaaac agagtgtcat    5340
tagcaatatg tcgtccaacg cagatacgcc gaccaaaacc gaaggaaacg tggcttcgca    5400
tagattagcc tatgtcgtat tgaaaaggca catgaacgaa cttctcttcc ttagtgcccg    5460
cgaccggagc gagttggcct gtctcgtcaa ggtgccgggc cggatcgaag tgttcggcgt    5520
caagtccata attctctggg tctctgttaa tatgccaaac attggcgatg aggatactac    5580
cggcctgtat atgtcagatg agtatgacag cagcgaactg aacgtcgttg acgcttacgg    5640
gaatgaagta tccgttatag atatcgtcct cggtcgaccg atgagggagc cctggaaaat    5700
cactgtcagt gtcgtgccac acgcatctcg agagtcatac gcaccaactg gatcctgcac    5760
ggaagacaac aattcgcatc aaacggagga gtcgagagag aaaacttacc actgcacgcc    5820
atctgagagt ctccttaacc attgcacgaa catacggtaa atgctcatag tctgagaaag    5880
cggggagtcg atctcgaccg acaaccttat cgagttctgc ttgggctcgt ttctgcgcat    5940
cagggtaaag gatcatagca agcatccacc aagatatagc ggctgagctc gattcggcac    6000
cagccgtgct accgaataat cagatgggag gaaactaaac gcagtctaaa agacgtacta    6060 catgcccct gccagccaag agctttcatg gtcagtcagc ccatgtcttc cggcgccttg    6120
aatcagagta gccacgaagc tgggacgatt attaccttcg gccttatata gaaaagatta    6180
gcactagctg tcgatcgcat catcggtaac gtactactcg atccttgacg ctgtggaaga    6240
ggctttcaaa catggacgaa tctttggcat accagccttc tgcctcccct ttccactttg    6300
cgtatctacc aaatcagcca tcagccgctt tcccgtgacg ttttgtataa ccttacttgc    6360
tggggatacg cagcatccag ggaaaagact ccacctttgg gttgcaggca tcaatcagac    6420
gctgggcttg acagatgaga gtctaaccca caaagtgagc accaggcata gcagcacggg    6480
ttaaccgtgc agcaaagtcg ttgatgcgct tgattgatgg gtcttgttcg gacgttgcag    6540
gcttatcgta tacgatggac atgatagtag aagcggcggt acggcgaacg tgcgataccc    6600
atcggttggg ttccgccagc aaatcgtttg caagaaggac agcttccttg atttggattg    6660
gatggtattg gttcacgatg ttttgttga gaccttcatg agctgcttta cgcatatggc    6720
gccagctaag ctgcgatatc aggtacgcat actggatcag tgagatcaaa agcttacgca    6780
ttcccataag gagcgaacgc gacgaacatg cctctagtca ttatgtctga ggcgacgatg    6840
ttgccgtggg ggtccgaaaa cttttgcacga tctaagagat ctgtggcaac cctcaggag    6900 ttgatgacta tgagaggctg tccggcgaca ttgaagtaca taaggtcgcc tagagcatag    6960
cgtgaaacca gaaatcatgc ccaaacgaag agcgcgcata ccatatttct ttcccagctc    7020
ggtaaatgtg agccattgtt tgctacgtag ctggagaaga ttgccaacga taggaaggcc    7080
tctaggtcca ggtgggagct tgcgccaaga gctacggatg cgacgaacga cgatgaaggt    7140
gacgatagcc acagcagcca gaaaccaagc agacgatgcg tgtgtcatca tggctcggaa    7200
aagaagagat agcgttggtg gttcttcttg atgtgaaaga ctaactcatc acgcgcatcg    7260
aatccctagg gtgagcgtca catttttcttc ccgccatcag gtttcacggg aaggtgttcg    7320
ccgctaacaa aggatatggt taagctcagg agtgtatgtc tggtcccaga ctttgattag    7380
ttgatatcat agtgctccta gaacagtctg ctggctcacc ttcgaaccca ttttgatccg    7440
agcgctgaaa atagttgaca gttgacagat gaaaataag tatcataaaa agtaccaaga    7500
```

-continued

```
cccccactta caaagttaga gggtgaaaat cctccagaaa caatatctcg ctgagctgtt      7560
ggcgacgtcg tggttgtgag ctcgatatca aattgactga tgtcatgcat ggacgtaatt      7620
tcaatatctg cagccacgtt gtgcgattgt acccgcaacg gcaaccgtcc tactggccta      7680
tggctagcac cgatgagtag aatgtagtat actagagctt tttgggagcg atggcatttg      7740
gtaaatatgg aaattatttg gaactttgta cctactctcc aaggaagcac ctcgtttcac      7800
atcttccaag aaactgtcct tgcttgggat actttaaatg aagggtttat aattcattct      7860
aaatccgatg acgcctcacc aacggtccac aggactttca attggctcat atcatcgttt      7920
ctcgacgaaa aacgtttccg aggaatattc gaatttcagt ctacagtaga cgatgtcatt      7980
tcctatagtg tcgtagtcgt agattttgta ttacttagag acaacagag tggaagggtc       8040 acgtactttt tccacttccg tgacgtattc cctgtaatac gcgtccttct cattatcagn      8100
aaggnngagg cacttagctt taacgacaat atccacagat tctacaccag caatatgagc      8160
ttcacctaac tccaacttcg tcttggcccc gagatggcaa aagtgagtgg ttacagctgt      8220
cgatgacggt cagacctatt cctcaattag tcctgtgaca gtattatcga tcgatgggaa      8280
gtgcaactct ggtcagaagt gcaactttcg ccaatgttag cctcctacag gccgcattta      8340
cgacttgttc ctcctgcaaa tttaaagtag agtacctata tgatacct acaagtatgt        8400 taagtcagat cggttttccg ttgagataat tataatcagg aatttctaca tcgtgcccaa      8460
tcgaaaaaaa tgaatagcac atcgcgttct tgcttcgtat cgatacagtg aaatgccggg      8520
tggttctgag agatttatac aagcttggta tatattttta gagtgttttg acaaaaacga      8580
atgcgagcag acctgaagta aagtttgcac atgcagtcga agctcagcat ggcaagctca      8640
gccgctccgc gcttgagccg atcgcggctt ggtcgcgatt gcggtgtacc ggcagcatcg      8700
gcacttcggg tcatatttcg tcgcagttgc acttacccgc tattttgacc caccacgacg      8760
gcatcactat tatgggttcg aatctcagac ggcgactcag catatttcgg caaggtctgg      8820
ctcagtgccg cagtcatcca agccgcattg ctgatgctgc aatcgagccg cagtgcgaca      8880
tatttgaaag atggatgcga gaccaagtat gtacgttgca aatagtagtg cgaaataagt      8940
aggtgaagtt ttaagcactg gtccacctgt gttgacttcn gnaagttgcc tctaagccga      9000
gtctcacccg tcggcaagcg agtcggttaa aaatcctaat taggtacagt aagatttgat      9060
cgacgcaaaa ttttcgatca tctcttcccc ccttctgcaa ttcgtttctc cctcatttct      9120
gagtcctttg catcggaaat agtatcgtta ggatgctgcg taagacaaga tggccgagtg      9180
gctgtggcta aggcaccagg ctaaggaaac aactgttatc aaaataactg cccccgacaa      9240
ccaaatcgat attcgagtgc cagtgaagag ttatctagtg tcgtgacttc ggctctgcaa      9300
ggaagcgaca ggaactttcc gtaatccagg cgagtacgat taccgttttt ttgaggttag      9360
agataccgtg ttgtaacata tgcatttggt gttcaggact tcgttttttg cattcaactg      9420
tatggatcga tatccagcga attacataac cacgtcgtcc ggtatcgata ttctgtgcta      9480
tgtcatcata tcccgtacga ccttttgact ctcgcggtgg tatgatatcg tgttttttcc      9540
gtcgcttaat ccaacgattc cttacaaggg gagccgttag aacctatgca ttacaaatgc      9600
gaagcagtaa ttcggccatt tctggcctca ggaagcccgt ttcctaggca tatctatgcc      9660
ccaaacccga ttagaggtga gctggctgct aacgatctgt ncnctgacat ctagtggcac      9720
tcaagagccg gttgatttcc attcatagct tagtattcaa caagggtccg ggatgccctt      9780
atgtccagca ttgaatggct tactgcatca ctactcacac gtaacaagga cagatggttc      9840
tgctgttcaa tcctgcttgc catgatagcc actccccaga gaatttgttt gtcacgaaca      9900
```

```
gcaaacacgg gcaagctaat gtgattcttt cgattgcaca tcaactcgtt cttcggtcaa   9960
atgtagcagt gcatatcacc tctttctccg ggaatgcagg tgttacgttc ggtctatatc  10020
tttcactggc atcaacttgg cttggaatgt gcattaatct agaaactccg gggtgccatt  10080
caccctacgg tatgctctgc cagtgactat gtccatattc atcctctcaa aagacccagc  10140
gaagaacctt cttacctgcg cctcggtcta cttcatgaac cactcacaaa gatccaagaa  10200
ctcgataggt accgtcggaa gtgggcttac tagcatcctt cgtatcttca tcccgtacat  10260
cccgcaaacg cactgtctct gtccagccaa tctgacagct gaatttcatc agtgtgtcat  10320
ttcagacaat gtcactccat gcggccctat tcttgctcca cttctcccgt tgatgagggt  10380
gactgcgaac tcaccgcaca gtttgatctt gctctatcat ccccatgagc ttgggaacgc  10440
acgtaatctt agatgagaag gatacccacc agcttgcgat ggggctgcgt atcttacttg  10500
atcgcgaaag aagggtccaa gtcatttgga agctagtagc acaaggcatc ctcacatgat  10560
atcctcggtg ccgacataga aagtgggcga gtgaaggttt ggncgaagat tgttgattgg  10620
ttggatatcg aaccttcggc actcctcggg tatcgtaacc tcgtatgtgt tgttaatcac  10680
tgcggagcaa atagcttctt cgaagccatt acgttctttg ctcagcgttt ggtccatcga  10740
gtatttagag cggggtccat caagctgttc tgtccgcgtg gtatgactgc tatggtgggc  10800
tgttgacatc tcgatggatt ctggaatctc attgaaaaaa aagactatgc agcgctggtt  10860
gaatggttcg gcgtaggtat ttgctaggta tttacagcaa caaaaatatt acgcttgatg  10920
acgcgtttgt gggtggttta tggctattta ggcggcgatc tcggaggcca tttcgtgcgc  10980
ttgaagtccc caaaacacgg tttatgacga tccgagcttc cttttcatcg tccacgaaac  11040
cgcccgctta cggtatgcaa acggctgtaa agaaattcat tacgactagt ctactatcgt  11100
aacaggtccc ccttaccacc gtcagctaaa agggagagag tagcatatat ttattctcta  11160
agaatagatc ttgatacata agctggtcac tggtcagacc agactcggag gttcaacaaa  11220
aacggatgac acacgtccac gtggctgccg aatcttcttc cgactcgggt atccatgcat  11280
tcatctccgt cgcgtagtca gcgtcaaaaa tggcgcatca aaagagagtg cagatatgaa  11340
gaccagaaat ctgtgggcgg cgcagctcag agctggatcg tgggcacaaa tttggacgtt  11400
ttctgcttca cttgacctca tctttctctc taagatttat tcattgattt atttcgacgt  11460
tgcaaacgca cacatgagag ttgtcaaact gcatagcctt catggaaggg cgttctcaat  11520
aaacaatact cggtgcagag ttatctacag aagcaaaagc taggatatgt gcctaggtaa  11580
gccattttca atttggattc ggtacatcag cgcatcagct caagctcact tacttgcgcc  11640
agattcacat caatgttccg ctcaggtagc agagtataac catataagcg attatacggg  11700
atggggactc ctgtacgtag gcaatcgaga ccagtgacat tattccgatt aaatgattct  11760
acagcggagt acactctaca tagtgaagtg agaaagaaac ctgatagtcc tcagtgatat  11820
ccaaggagtt ctcgctcttg ttctactatt gcctgagctt cccggaacct tggagttatc  11880
ttggccttga aagggactgg acgactgcaa cgaagacgat taacaacgac ttgaacacgg  11940
aacagtgcag gacttacgtg actagtccat cttcaacgca tccgtcaaca tccaacggga  12000
ggggaacacc attctcgtcg gtagcacgtt cgatgttcat agcccaaagc atcattgcta  12060
tgtcaatgaa caaagagttg tttgcaacgt gccgtcccac acaaatccgt cgcccaaatc  12120
cgtaggtgac gtgactgcac aaattcagct tattatgtgt gggaactgga tatcaacgaa  12180
cctctcctcc ttcgtgtctg cgggtccagg ggccagcttg ccgtccttgt cgaggtgccg  12240
```

```
ggcagggttg aaatgttcgg catcgggccc atagatctct gggtctctgt tgaggtgcca   12300
gacgttggcg atgatgatgg taccggcctg tggtggatga gcacgtactg catcgagcgt   12360
aatccacact tacaggtatg aagtatccgt catatacatc gtcttctgtc gatgtatgag   12420
gaagccctag agaccgacta tcagaatcag gcatatctgc ctcgagagtc atacgtaccg   12480
actgggtcct gtaacggcag cgtcaattgg tctgcgttgt tcgacaccac ggagagagcg   12540
gacttacaac catgcgccac ctgagggcct ccttgaccat tgcacgaatg tatggcaaat   12600
gttcatagtc ggcgaaagac ggcaaacgat cgcgaccaac gacagcatcg agttctgctt   12660
gtgctcgttt ctgtgtttcg gggtagacaa tcattgcaag agtccaccag gacataacac   12720
ctgaagtggt ctcagcaccc gcagcactgt tgaagcttta gaggaggaaa tttagaagac   12780
gaagaagacg tactacatgg tcccggccag ccacgaattt tctctgtcag ttaaatcgtg   12840
tcttcccgcg tcctgaatca gagtactcgc caaactggga cgctcgtcac ccttggcctt   12900
ttcgaaacgc atgggtatca actatcaagg attcaatggc tgtgcacgta ctacgcgatc   12960
cttgacaccg ttgaagagcc cttcaaacat cgcagaatct ttagcgtatg attcttctgc   13020
ctcacgcttc cactttgcgt acctaatgag gaaattgtca atgcacgctt acgcaggacc   13080
tcatcaaact cacttgctag ggatgtaccg catccaaggg aagaattcca cctttggagc   13140
cacagacatg attaacggga aggaaaaccc gtagagagaa acttacgaag tgggcgcctg   13200
gcatagcagc gcgagttaat cgtgccacaa attcattaat gttcttgact gatggatctt   13260
gttctgaagt tggaggcgta tcgtatacca tggacatgat ggcagatgcg gcggtgcgac   13320
gaagatgtga attccatttt tcgggctccg cgagcacgcc agccgtaaga agaacggctt   13380
ccgcagtctg aatgggatga tatttgtata cgacacccct gttgagacct tcgtgagccg   13440
ccttgcgcat tcggcgccag ctaagtttca aatgtcagat ggaggaacng aatacgaagt   13500
ggaaggacct tacacatccc catagcgggt gaatacgact aagtttcctc cagtcatgat   13560
gtcggacgcg acaatgttgc gtgggcggtc ggagtacttt ccagcgcgac ggtcaagcag   13620
gtcggctgcc accttctggg agttgaggac caccagcggc tgcccggcga cattgaagta   13680
catgagatcg cctagagcca agtcagctaa tctacatctt acgcagctcg aaagaacaga   13740
ccatattttt tccctagctc agtaaacgtg agccattgct tgccacgaag ttccaaaagg   13800
tttccgatga gaggaaggcc tcttggtccc gggggaggt tacgccaagg gctgcgaagg    13860
tagcgaacgg tggtgtaggc gacgactacg attgcagtca aaatccatat cggcgacacc   13920
tcctctgaga atatccgagt catgacggct tatttccgac aagaaataat cttgaaggat   13980
ttgagagaaa ggggggggg gtgataaact cgtcctgtgg atgccgtgtc tctcttgtat   14040
ggtttatttt ctcacacctt agatccactc tattaggtat tacaccgctc atggatctgg   14100
aagctcggcg tcagtgctta ggagcgaggt aatgattcgc ccggtttgtt tcaatcactg   14160
atcagaacaa catctgagtt gatcggggtc tgatctgatt cgttgcatac ccctggttcg   14220
atatccccgg gccgctacag cttcaatatt atgtatttcg gatatcaata caatgttgac   14280
agcttgagta cacatctgct ccgagcaccg agttcgagaa aagataccaa cttccccgta   14340
acggtagata cgcgcgtagt aacggcatag gnagacgata ggtacttgtt attgcnttac   14400
ggtcctacat ttgccatctc atcggctcct nagccacacg gccactatcg gagtcgcgaa   14460
agcatgtagc accnttattt ggtntgcgcg attttcggca tacgatggat ttcgctgagt   14520
caaggtcaca gtcgttggag gcattcggag accctggttc gcttggttta caaaatggga   14580
ggacacaagg tattgtgtgg agccacattc ataatgtaca atgttaatac tgtcttggcc   14640
```

```
ttatcgacaa tcaatcttct cattcaactt cggtaacttt tgactcttct cgggcggcca    14700
tggcggcaat cccacgattc acggattcta gacgtaatct actcaatgcc tctagctgat    14760
aaatacgtag ctgcagttgc atagctccgg tgtaggcacg ctgaatttta agttgaacgt    14820
gctttgaggt gtttgaaagc cactggaaac attatgttcg atctgatagc agaagttcgt    14880
aagccagctt gagactcggt gacagttggc gcactgagcg ctctgatgta acaaagccgc    14940
agactccacc acccatgagt aagatcgtga tttcagcaat gctagcagta cagactctac    15000
gcggatattt gtcactagta acaaaatgac tggttaacaa aggcgtcaca ggacagagcc    15060
tttcacaaac agcaagagta aggacatatc aagacgacaa actaatagta ggatgaatcc    15120
acacaactct cagtcgaaca caatcccgcc atcgacattg atctgattgt cccatttaag    15180
tcacaatagc aaccataatc acaaaagagc ttactgtttg tcctggtaaa agaacaatgt    15240
caaaatatag ctgatgacga gaaggaaatg cataccggtg atgagacttg cctccttgga    15300
tgcaaggaag gaaaccacaa ctgcgatatc ctcgggcagg gcgatgcgac ccaaggccgc    15360
tgttttatta agcttcgaaa gtgtaagata tgacgtgatg aaagtgaaat tgacgcacct    15420
cttgctcaag aactcccttg ggtgtgccta taatggtttc gaagtgatca tctggaaata    15480
aggagaatgt cggtataaag tagaatagaa caatgctctc gttcatacac ataggtgtct    15540
tcactggccc tggggcaaaa gcattgacgg agattccatg aggaccgaac tccaaagctg    15600
ataaaaaaag tattcatgag cgggaacctt tcatatgtat tcgacggagc tcacccgcaa    15660
cttgggtcag tcctcgtata ccgaatttgc tggctgcata tgcactgaac agcggttgac    15720
ctgaagatct atcaagatag atacagatta ccgcaacga ctgctcacct ttcttcccgg    15780
ttcccgaaca cgcgcctaga atatcattga cggggaagct ctgaagacgt cgacatacag    15840
cttaccgatg atcctcccac ctttccttg agtgaccatt tgtttgccgg cgtgcttgta    15900
gcataagaaa gtaccacgca ggtttacaga ggtaatgcgg tcaaagtcct cggcagtagc    15960
taggtgacga tgagaaatct ggaagaaagg gagctatgaa atcgtactat cgaaaaaga    16020 cttcataatg gatatcccag cgttgcagga ccatcttgga gaaatgagat ctcgtttgcg    16080
acaagcaaca gccgaacgta ccacgtcgag tccgcctaat tcttcaacaa cttttgaaat    16140
catctcttca acctcggttt cctgcgagac gtccgcaaaa atgtagcagc ccttgcgacc    16200
aacggcctct atagcggcga gcgcagaaac gaggttcgct tcgtttgctt gaagatcatt    16260
gagcgcgacg tcaaatccgt ccgatgccag tcgaagtgcg atggcacggc caatgccctg    16320
tccagcaccc gtgacaagcg cgactctgcc ctgagaaact gaagtggacg ccattgtgtc    16380
gaggagaagt ataagggagt aatggcccgt ggccaccttt atatatgatg gtcataggat    16440
aaggtcagca atcagtcgtg tcgagttagc ggtggttcgg ttcaagcggt aataataagg    16500
cctttgccaa acatgtgtaa tgtgctgttt caaattcgaa gtccatctac ttgtcatcta    16560
caccgtctac actgtgaaat attcctcgaa actaatttac tctaccctaa tatataatat    16620
atacagcgca aacgtactcg ctagagatga aatccgtcaa caatttgagg accaagttcc    16680
tccgacacca tcttgggcat cagcgttatc cacctcctct ggatgatttc tggacccttc    16740
tttccaaagt atctctcgct ctcgaagctc cactggtcat tcgctctcac ccaattacct    16800
agcccatcac agtatcgagc aacctgcagg tcaatgggac ctccccatct gggcactttc    16860 ttgaagttttt ccatgaacct ggactcgagc tgcttgtggt attcgtcgac ccaaatcatg    16920
gcacctgcca cgtctgtcct gagctcgttc attgcgatag tgacgatgtt gtggctagag    16980
```

```
accgcgtcag aatgataatg acgggcgaaa tgctaaagac tcacccgtcg tcatcccgag   17040
cttgttcaag gttatacgaa acgacatcct tgaaagtata agaggtcagt tccctttttc   17100
tgtggtggat aaagacggat tgctcacgtt tcccaagcag agcatatcaa tacagctctt   17160
tctcaagttt ctttgataac cggatgattg atgactttcg tcgggtaact gcatgtcaaa   17220
ctcgagaagt gcgaacgatg gtttcgcgcc gatggtgttg cggcgaactt cgaggtacga   17280
ctcgatgcct cggacgtggg agttgttgcg gtcggcggcc tgttgtacga cagactccag   17340
gtactcgtcg aaggtgtcga tgaagcgctt ctgcgcttga gtgctcgctg tcttctttgc   17400
gaggtcccag aatctatagc gtacgatcag tccatggatc atgggtatct aaatgtgtgg   17460
tactgactgt cgagatactt ctcctccaat ccactctccg gcgggccgag gcttctctgt   17520
attccgaatc gcatccatga ctatgtcctt ctgtgcgcgc actggataca acagtcagaa   17580
taactgttat ctcaaggaga atttaatggt gagcttacct tcctcctccg tcgagacgtc   17640
cgagtactcg tcgataacga agaaactgtg tgatcgcatc aacaaaatat ccccgagcgc   17700
tggcttgaag acctacaggt tcatgagatc acacccgcta cggagacgtg ctagagacga   17760
aaaaggatta ggctccatgg acgggcagtt ctcctgcatc actcgccttc gtccgccagt   17820
gggtacgcga atgaggccag gagatctgag tgatggtgta cagtcagtct agctctaata   17880
agcgccgtag tcttgactta ctgaagtcgc agcggtcgaa agcttcctga gccttcgttt   17940
ggaaagccta acgtcttggg tcagaatatt cgacataaac gtattctact ccaacttac   18000 tcggaagctt tttgcccagg ccgctgatgc cttcttgact tcggcatagt gggggttgag   18060
atggcggggc cattgccagt tggcaagagt atcaggaagg aagatgcgtt gagacattga   18120
gaatagtgga agggtgtggg gatttctgca aggtcagtct ggaacgctct taaggtatgg   18180 ataattacc ggtcatttta aaaggcaatc ggagatgaac ggcttgcgat agcctgaatg   18240
aaacccgttg caaagcccat agatggcact ggttcacgag attcactctc attccggttg   18300
ggaacttctc tatgtgccgt agctaccgtg cctcagtgta acataagccg ggcgcgacct   18360
tggcgtaact ccggtatcta actccatacg atgatccttc aagcgccact ctgcgcgaac   18420
attcctgcgc ggagttggaa atgcaccatga aaacggaaat gccgcctcac ctctatgcca   18480
tgacatacga atttgaactg agattggtcg ttcattgaat atgtttagct atagtgaaca   18540
taagaacagg gcgaatattg tttccctcac cctgggtcga tgatccatga tcggcgttct   18600
ggtggtttta cactgtttca taacgctcct gtatcaacgg taagtcggcc tcatcgcagc   18660
ggctcgcaat catcctcact gtnttgactt taggcgagtc tcgacgttgc gaagcggaag   18720
tgcaaaagta aaagtgttaa aaaaggccgg tgtattatgc aagaacggag tcgaatcaaa   18780
agtaccaaca gacttcttca atattcactc cctttcggtg agagcggtcg acctaccgtg   18840
acgacgatcc gtggcatgtc agcgtctatg gacccgaact tagcgccagt ttattgatga   18900
aactagcgtc tacttatcgg aaattgttta aataaaggat tgtatgagcc gataagtagc   18960
attcaggcta tgcacatgcc tccattggtc ctcggcatct tgtgagagtt cagggtacac   19020
tctcaaagtc ttgcgtagta ttccggcaga tataacgata accgatctga tccatcttcc   19080
acgcatcttg atgctaaagt aatataccac acttaccgcc gcctcagcgt ctgattcatg   19140
agagtttctc gctgactaat aaccttggaa gtattcgagc tcctaccgac cttccggcac   19200
cgccactaga agcatactgc gaaccatagc aaagtctcaa ccgcccaggt acattcacac   19260
tgattaggga atttagtgtt ccgtagctcc agttggaaga aacagtgcca ccggaaccga   19320
acaattgacc acgcgtacta cttagtctaa gtgggaatct cggatcgatc attgatccac   19380
```

```
aaaaatcgaa aatactcaag tatgtagttg acatnnaaga aatgatcgtg caataattca    19440
agaagctcgt caaaagcgtc aaaatcggcg ctcagagccn attcacgaga aattttgcca    19500
aatcagctgg actgagggcg agatgttcgt ctattccaac ccgaaaccct gaggtggacg    19560
aaaggcggac ggcgatgcat gcggaaatga tggtacggat aaatggcaac gccggcccng    19620
gttagcgtat tttgcttttt acctccgccc ttgtcgaaca gctgagcagg gccttgttct    19680
atgaaatttc acctttgaaa agagatcgtt acaggatgtt tgntgtggat cagttcatgt    19740
ttcgaatctg cacccggccg gtgtcggtct cgatccaaac ccgcgacatg gaacctttcg    19800
gagcaatggt aactgattac tgtagtttcg acccaatggg tatgcctctc tgtactttcc    19860
tatgtaggca aaccgagcat cgggaaatag tacatctcca gggtgatttc acctcctcgc    19920
ttcctcctcg tcatggattc tgcgtctctt gccgttgtcg tttgggctat ccttctcgtt    19980
ttgtggctca gaaggatttt cggtcaacgc tcttccctcc ctctcccccc tgcacctcct    20040
ggttatcccg ttataggcaa cctgcttgac ttggctaaca atgacgtgca tatcagagcc    20100
aggcactggt cccgcaattt tggtgagtct atcgtgcaag ttaataacag tgaaataaca    20160
gcttgtatct tcagatgacg atgtcatctc tctcaaagtt ctgggaaaga ccatgataat    20220
cttgaactcg cccaccgcag tctctgatct cttttgacaag cgagcctcta actactcaga    20280
tcggcctgac atgccaatga ttgttgactt gtgcgtaatt tctgacttac tcgtaacaac    20340 cttttgacacg ttattgatca ggatgggtgc gtctcaccgt gatgcggtac aagagcaact    20400
tttatgagat gttttccgta taggatggga ctggacattt gccctcatgc ggtacgggcc    20460
gcgttggaag gaacacagac gggtcttcaa caaccacttc aatattggca cttctggtgc    20520
gtcagaagac cggcatattc agctacgcat ctgtcgcgag ctcttgtcct tgatgttcca    20580
atctccttcg aaataccttg agaaccttcg gcagtacgtc ggtgtggttt ctggaagaga    20640
ccgttcctta tcgacttcat tttctaagct acacaggtca tattattctc aaacgcacgt    20700
atggacacac ggtagtcgat gagaaggacc cttatatccg cctggttgag gcagcgtccc    20760
aaagtacatc tgaaggtaat tcacttcctc aaatttgtct taatgatggc agttctcata    20820
agttttgtag ccgcagtccc aggagccttc cttgtcgatc tattcccatc gagtacgttg    20880
ataaaattca gtcattcagc ctgccaatat ctgttctgta gtgaagtata ttcctgagtg    20940
ggtcccgggc gcgcaattca agagaaaggc tagggagtgg taagggtctt ctgttgatat    21000
tcttagctct ctccatttat gaactggacg ctataggcgc aaactctcag aagctatgat    21060
caacgcaccg tatgacatgg cgaagggggaa atttgtatgt tcaactttga tcggatcacg    21120
ctgcgaacta aattctgttg catcgtgaag gatgaaggaa atgccgaacc ttgctttgtc    21180
tctgcttgtc tcgagcagaa caagaccgct tccggtcaag ggttgagcga agaactcatt    21240
aaagacaccg ctgccgtcgc atatgctgcc ggtcagtttg tctctatttc gtttcgcatc    21300
cctattctca tgaacttgat aattaggtgc tgatacggta caattcctct gggccttcat    21360
tcgacttaca acacttacaa attataacag agcgtctcca ctctaacgac atttattctc    21420
gccatgacac tttatcccga tgttcagaaa gcagcacaag ccgaactcga tgcattactt    21480
ggcggcgaac gtttacccga ttttggcgat aaaactcggc tgccatacgt cactgcaata    21540
ttaaaggagg tccttcggtg gattcctgtt ttaccgatgg gtgagtacga gccgggtttc    21600
ttaatttaca cgacccaacc acgttttagc cgtacctcac cgagccgtta atgcggacac    21660
ttacaaagga tactacatcc cggctggtgc cttcgtgtac ggaaacgcat ggtgagtcta    21720
```

```
ttgtcgacat atgaatgctg cctaaacctg tgctagggct atccttcata accccgacat   21780
ctttgcagac cccgagacat tcagaccaga cagattcatc gagaacccaa cgttactcaa   21840
cccgatagac aatgggtat ttgggtttgg aagacggtga gcaggaacat cattgtctcg    21900
ttccagaatt gcctaatttc atcaacagcg cgtgtgcagg gagggtaatg gcgcttgaca   21960
ccatgtggat agccatggca tccattctag ccgtcttcga catttcgaaa gccgtcgatg   22020
aacgcgggaa tgagatctca cctcccgtaa agctcagtcc gggaacgata aggtaagcgc   22080
tgttagataa agactacatt tctggctgac cgttgttgct atcaaaagtc acccggcacc   22140
atttccgtgt attatcaaac ctcgatctaa ggctgccctt gaactcatta cgcaggatga   22200
ctga                                                                22204
```